(12) United States Patent
Ahn et al.

(10) Patent No.: US 11,800,864 B2
(45) Date of Patent: Oct. 31, 2023

(54) COMPOSITION FOR INHIBITING ICE RECRYSTALLIZATION

(71) Applicants: SEOUL NATIONAL UNIVERSITY R&DB FOUNDATION, Seoul (KR); Korea University Research and Business Foundation, Seoul (KR); PUKYONG NATIONAL UNIVERSITY INDUSTRY-UNIVERSITY COOPERATION FOUNDATION, Busan (KR)

(72) Inventors: Dong June Ahn, Seoul (KR); Ye Dam Lee, Seoul (KR); Do Nyun Kim, Seoul (KR); Chan Seok Lee, Seoul (KR); Sang Wook Wu, Busan (KR); Su Hyun Park, Busan (KR)

(73) Assignees: SEOUL NATIONAL UNIVERSITY R&DB FOUNDATION, Seoul (KR); Korea University Research and Business Foundation, Seoul (KR); PUKYONG NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 893 days.

(21) Appl. No.: 16/702,221

(22) Filed: Dec. 3, 2019

(65) Prior Publication Data
US 2021/0161125 A1    Jun. 3, 2021

(30) Foreign Application Priority Data
Dec. 3, 2019 (KR) .......................... 10-2019-159420

(51) Int. Cl.
*A01N 1/02* (2006.01)
*C12N 15/11* (2006.01)
*A23L 3/375* (2006.01)

(52) U.S. Cl.
CPC ............ *A01N 1/0221* (2013.01); *A23L 3/375* (2013.01); *C12N 15/111* (2013.01)

(58) Field of Classification Search
CPC ......... A01N 1/0221; A23L 3/375; A23L 3/37; C12N 15/111; C12N 15/11; C09K 3/24
See application file for complete search history.

(56) References Cited

U.S. PATENT DOCUMENTS

2019/0069537 A1    3/2019  Wei

FOREIGN PATENT DOCUMENTS

KR    10-2010-0110778 A    10/2010
KR    10-2018-0084782 A    7/2018
(Continued)

OTHER PUBLICATIONS

Park, Sung Ha, et al. "Three-Helix Bundle DNA Tiles Self-Assemble into 2D Lattice or 1D Templates for Silver Nanowires" Nano Lett. Mar. 2005, 5, 4, 693-696. (Year: 2005).*
Sigma, Technical Bulletin, M13mp18 Phage DNA, Single Stranded (+Strand). Product No. D8410. Date Mar. 2005 (Year: 2005).*

(Continued)

*Primary Examiner* — Christopher M Babic
*Assistant Examiner* — Thomas R. Amick
(74) *Attorney, Agent, or Firm* — Sughrue Mion, PLLC

(57) ABSTRACT

The present invention provides a composition for inhibiting ice recrystallization, including: A nucleic acid structure comprising a scaffold nucleic acid folded at predetermined positions to form a plurality of strands, and a plurality of staple nucleic acids, wherein at least a portion thereof has a complementary sequence to at least a portion of the scaffold (Continued)

nucleic acid, thereby binding to the scaffold nucleic acid to form a double strand. Therefore, it is possible to increase a survival rate of cells due to having excellent effect of inhibiting ice recrystallization upon cryopreservation of the cells, and maintain a texture of food even when using the composition in the freezing of food.

6 Claims, 29 Drawing Sheets

(56) References Cited

FOREIGN PATENT DOCUMENTS

| KR | 10-2018-0108125 A | 10/2018 |
|---|---|---|
| KR | 10-2018-0109237 A | 10/2018 |
| WO | 2018/152054 A1 | 8/2018 |

OTHER PUBLICATIONS

Rangnekar et al 2011 Nanotechnology 22 235601 (Year: 2011).*
Communication dated Sep. 11, 2021, issued by the Korean Intellectual Property Office in application No. 10-2019-0159420.
Romà Suris-Valls, et al., "Marine Fish Antifreeze Proteins : The Key Towards Cryopreserving The Winter Soldier" Tu Delft Open Access Journal Superhero Science + Technology, Apr. 2018, pp. 1-12, DOI: 10.24413/SST.2018.1.2105 (12 Pages).
Communication dated May 20, 2020, from the European Patent Office in European Application No. 19213224.9.
Paul W. K. Rothemund, "Folding DNA to create nanoscale shapes and patterns" Nature, vol. 440, pp. 297-302 Mar. 2006 (5 Pages).
Office Action dated Mar. 15, 2022 in Japanese Application No. 2019-219641.
Communication dated May 2, 2023 issued in European Application No. 19 213 224.9.

* cited by examiner

[FIG. 1]
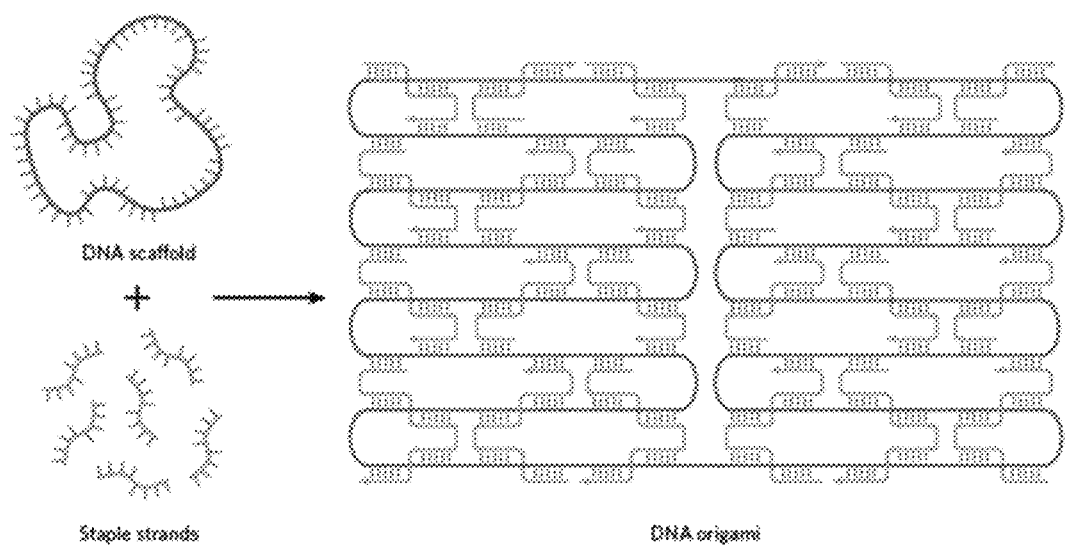
[FIG. 2]
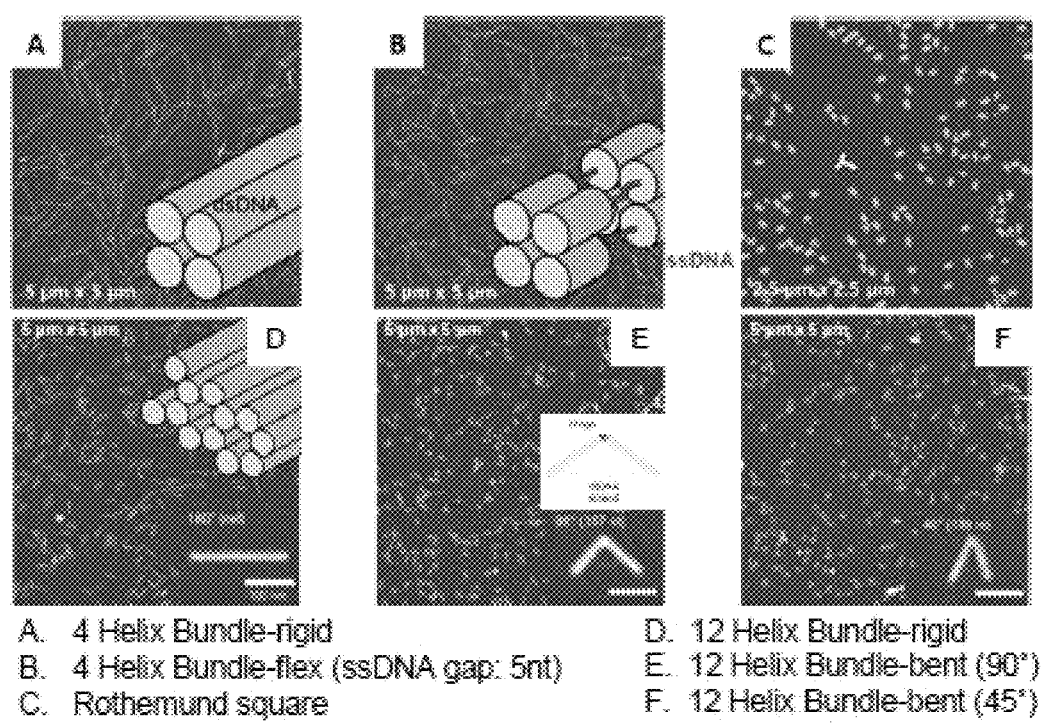
A. 4 Helix Bundle-rigid
B. 4 Helix Bundle-flex (ssDNA gap: 5nt)
C. Rothemund square
D. 12 Helix Bundle-rigid
E. 12 Helix Bundle-bent (90°)
F. 12 Helix Bundle-bent (45°)

[FIG. 3]
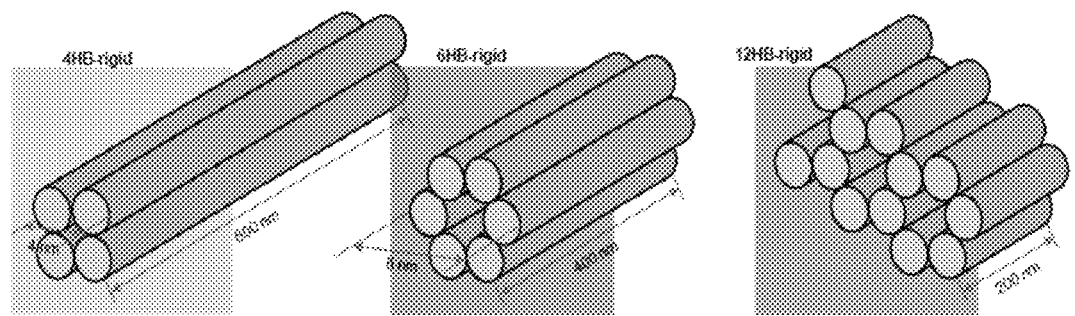
[FIG. 4]
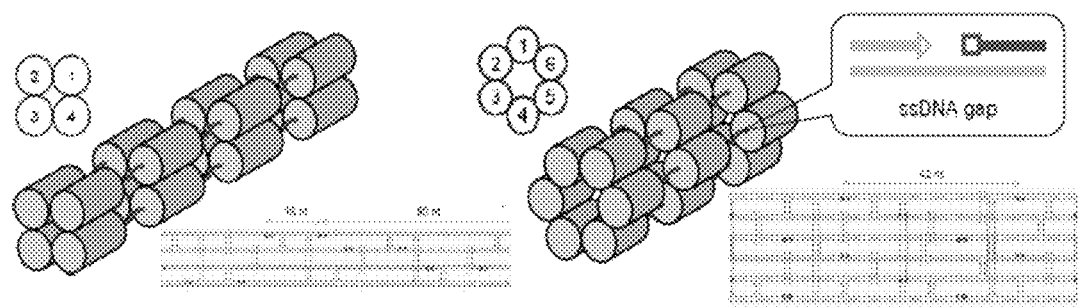
[FIG. 5]
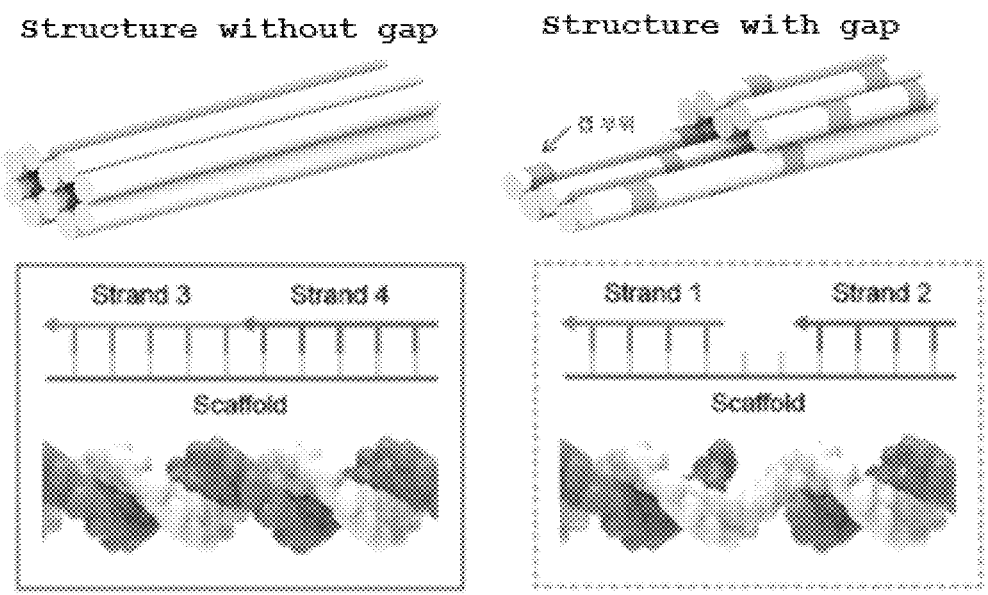

[FIG. 6]
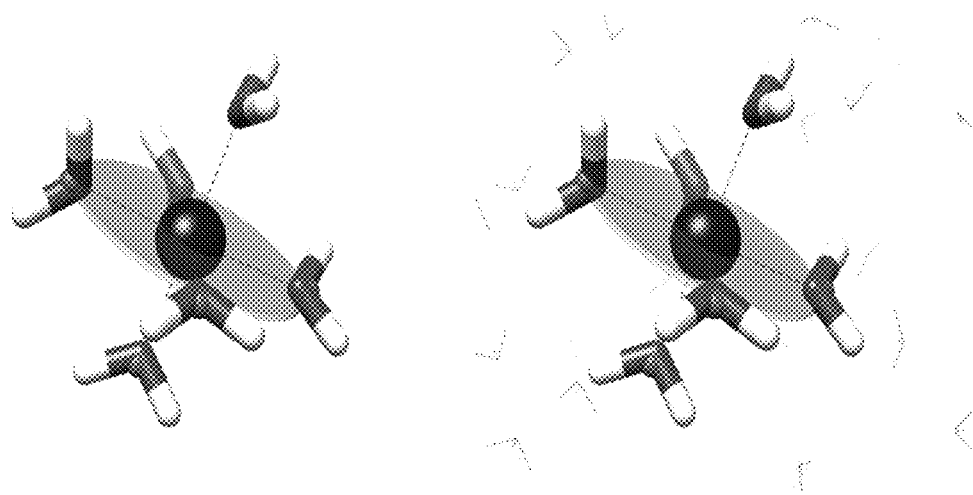
[FIG. 7]
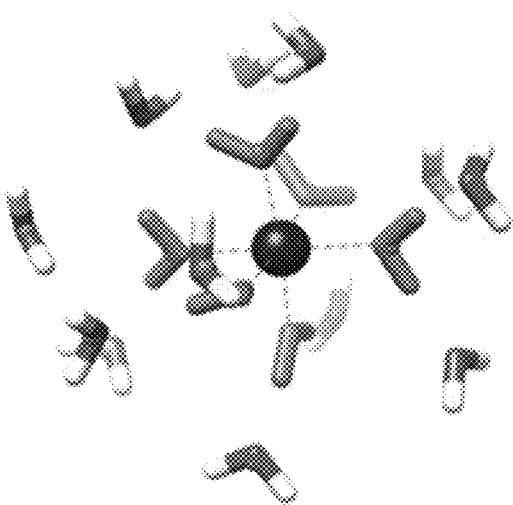

[FIG. 8]
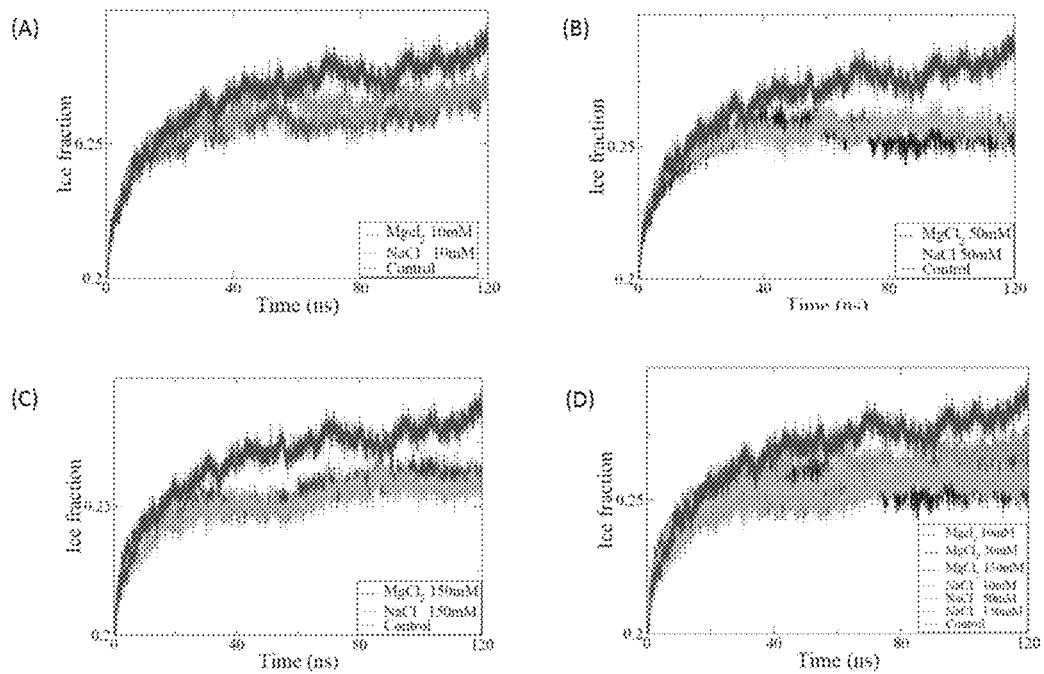
[FIG. 9]
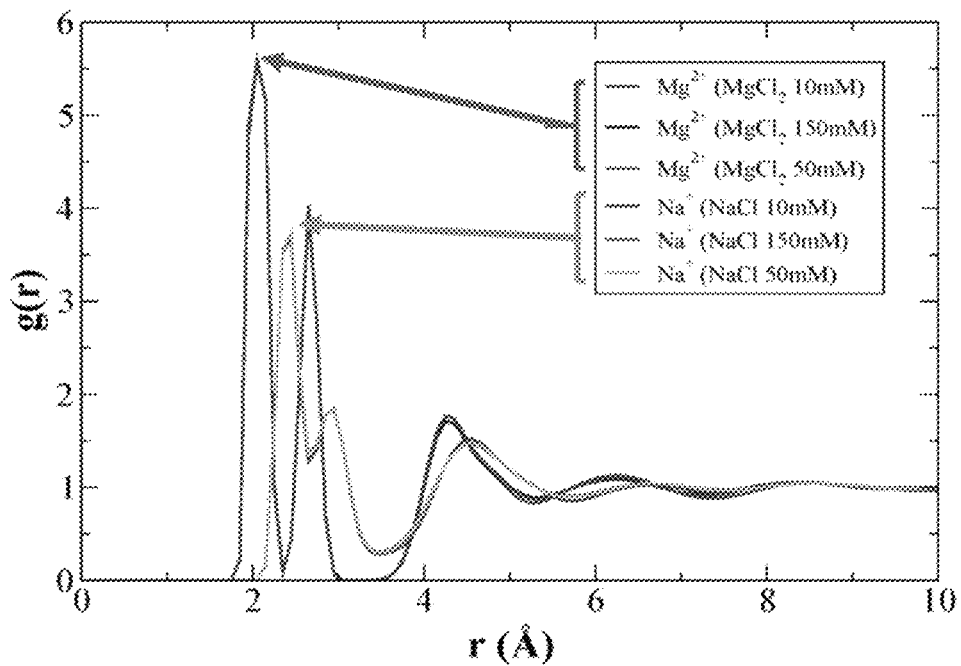

[FIG. 10]
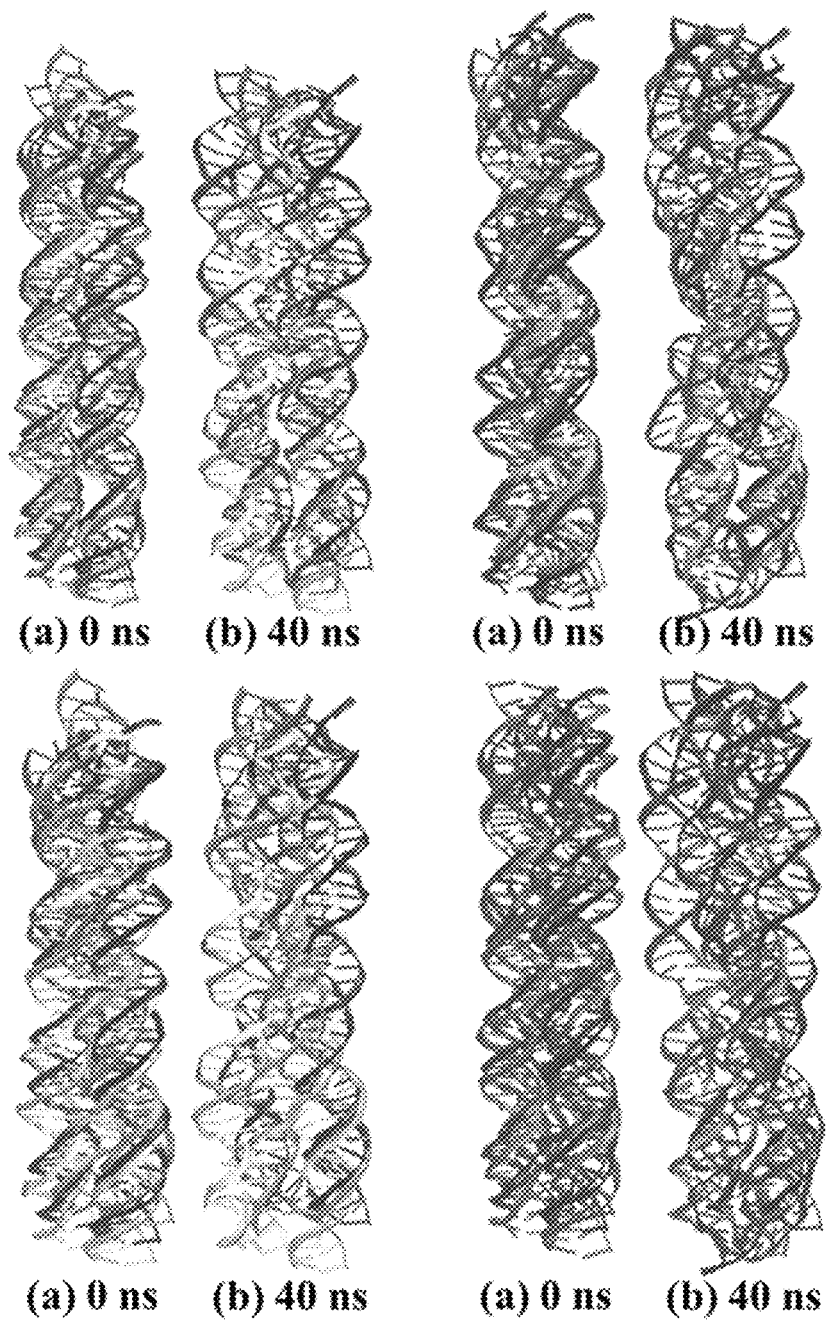

[FIG. 11]
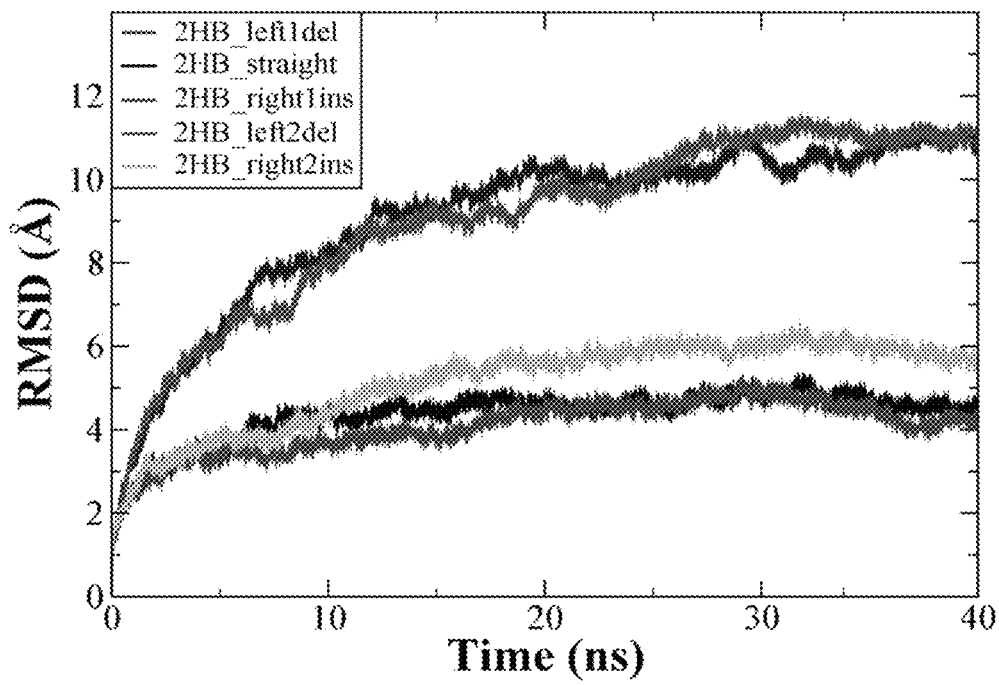
[FIG. 12]
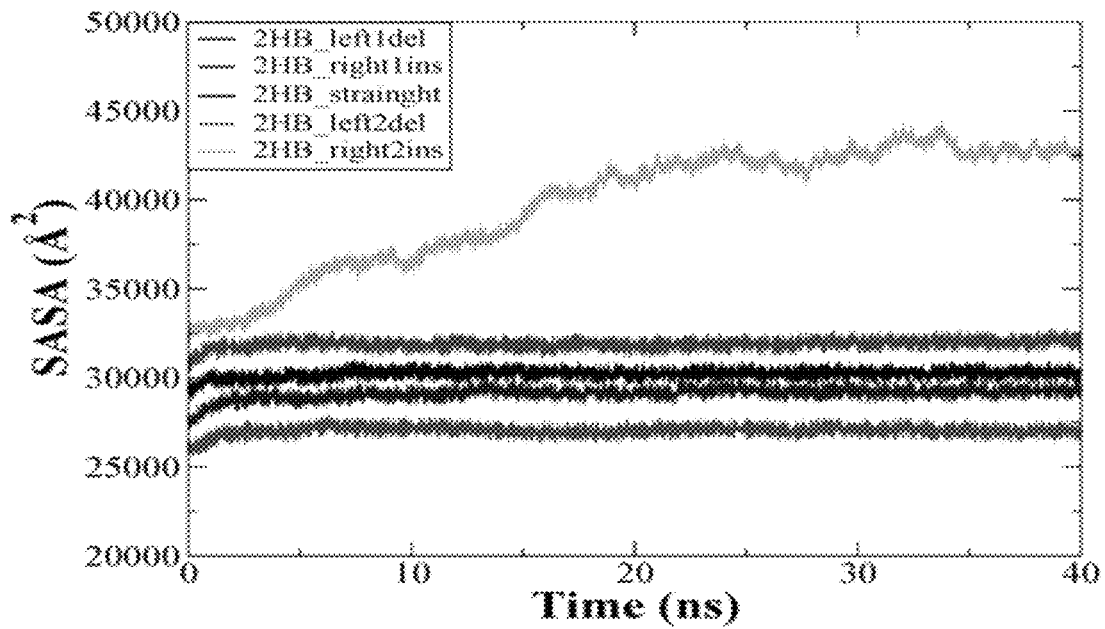

[FIG. 13]
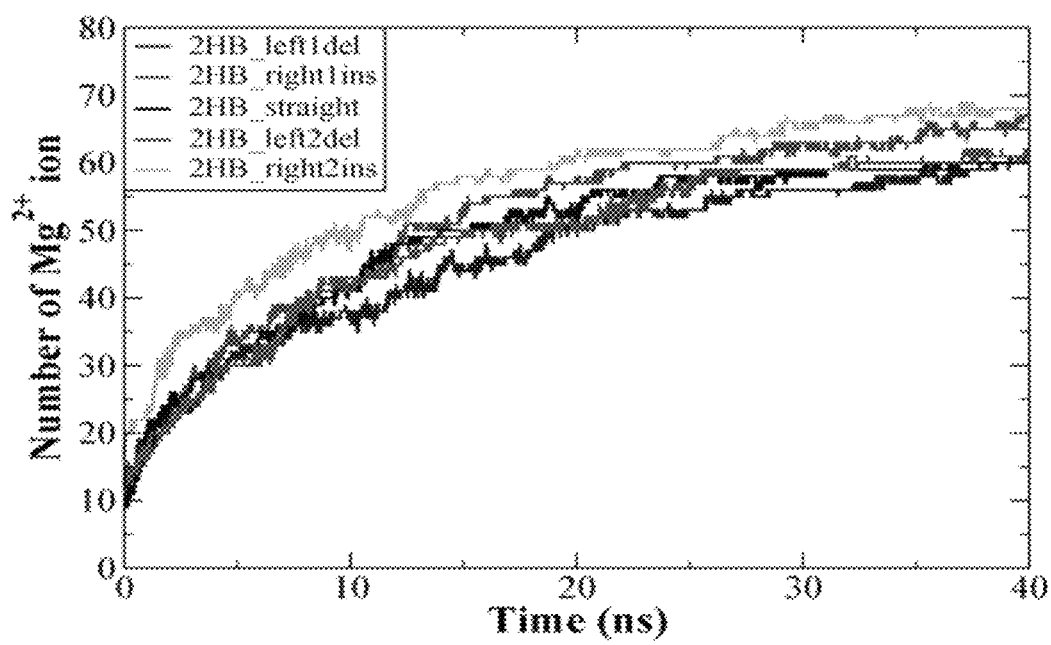

[FIG. 14]
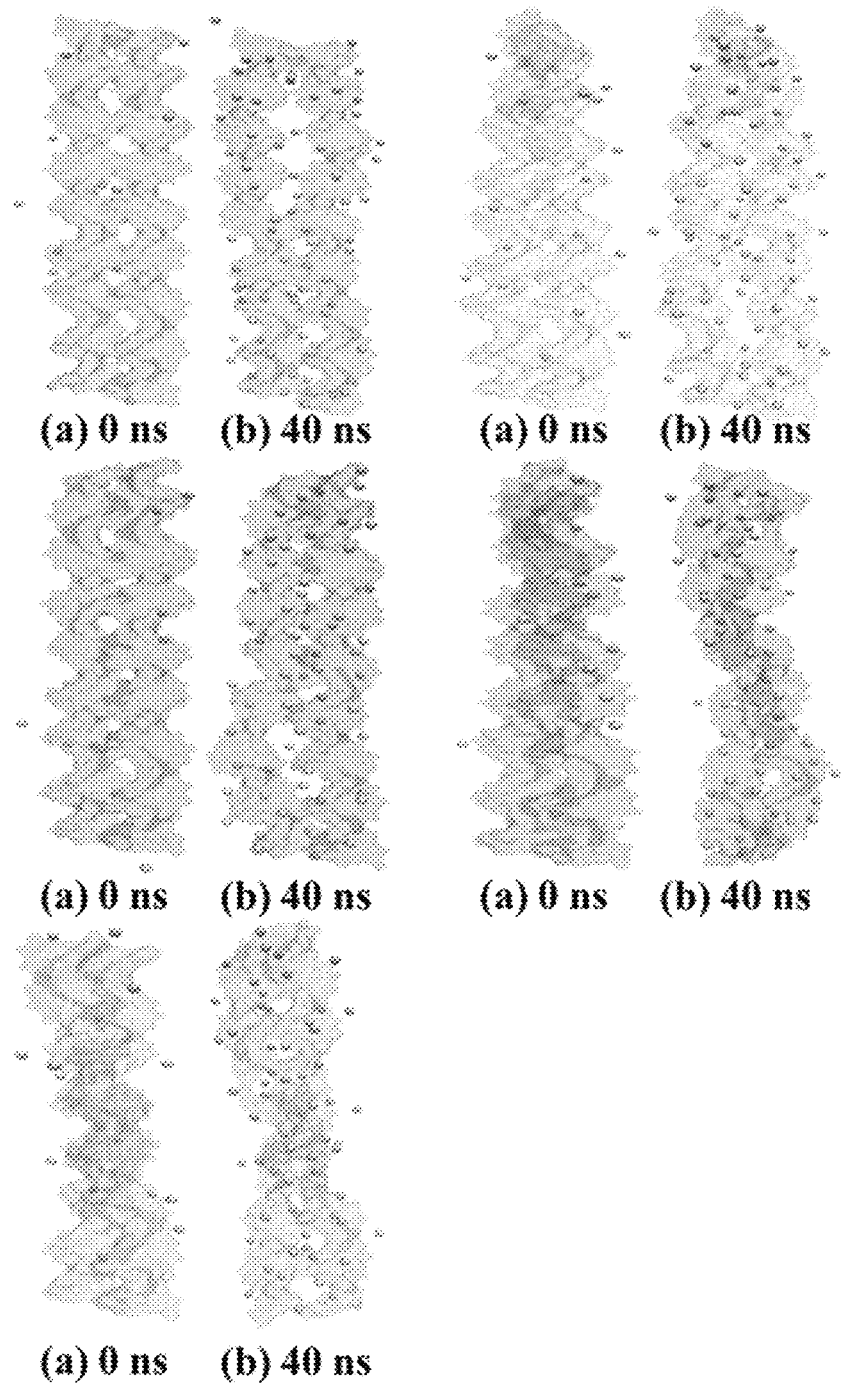

[FIG. 15]
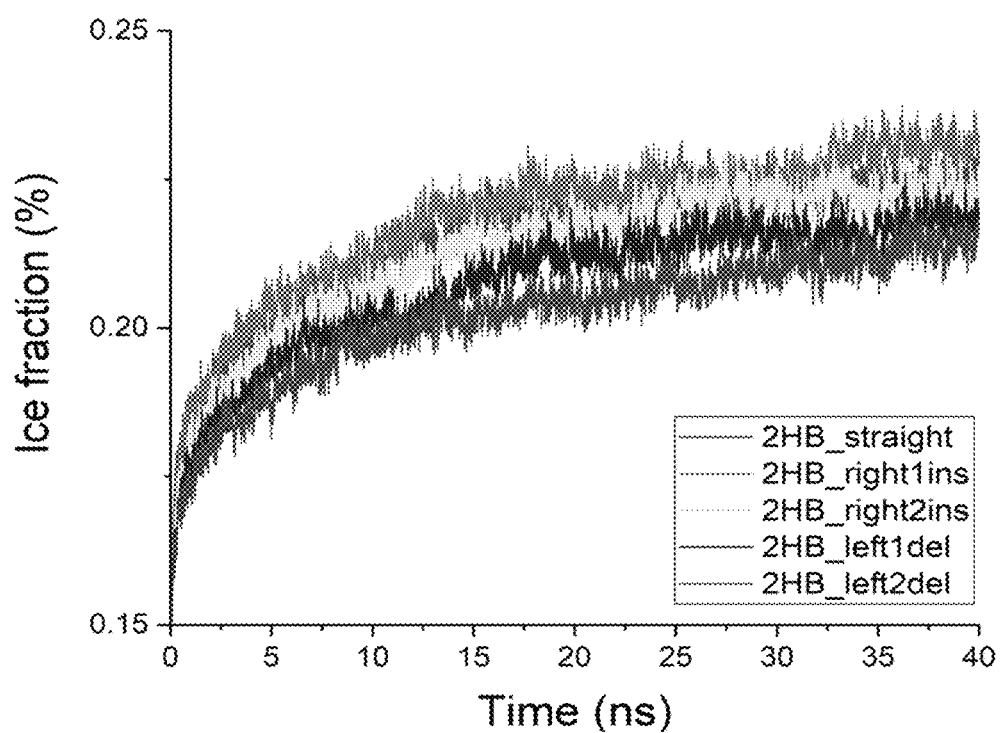

[FIG. 16]
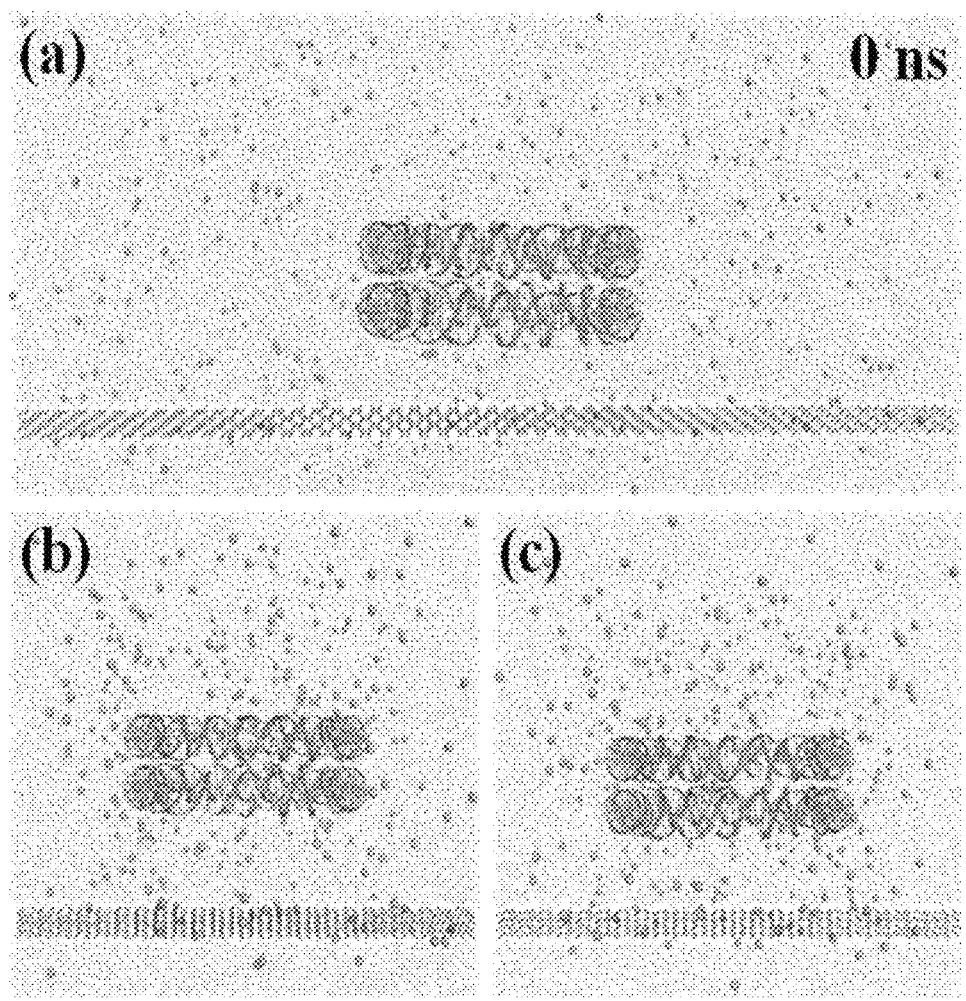

[FIG. 17]
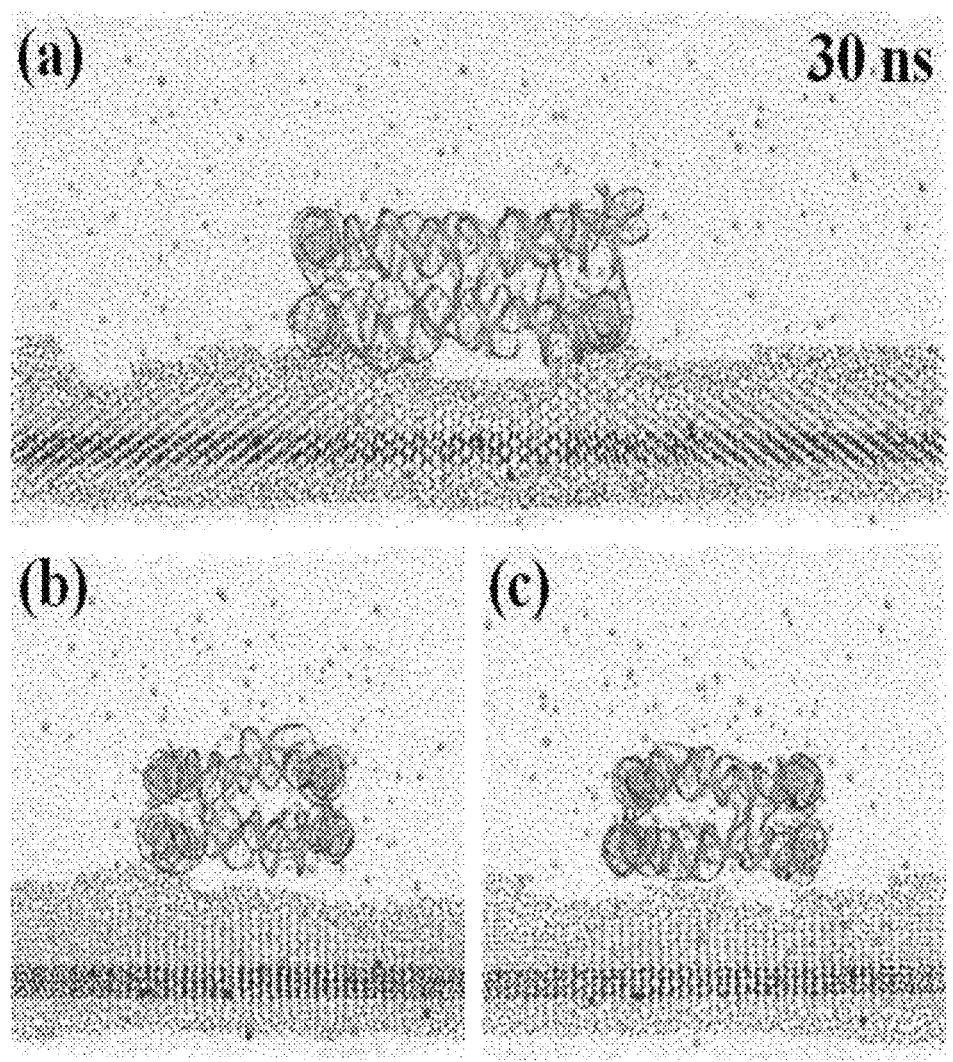

[FIG. 18]
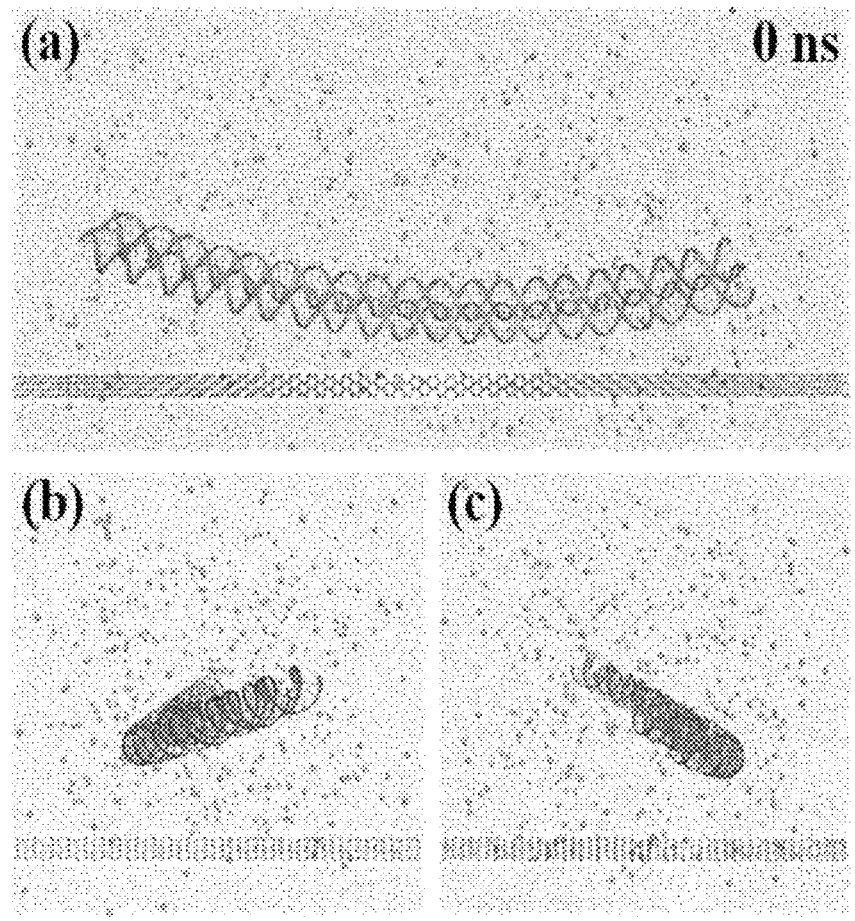

[FIG. 19]
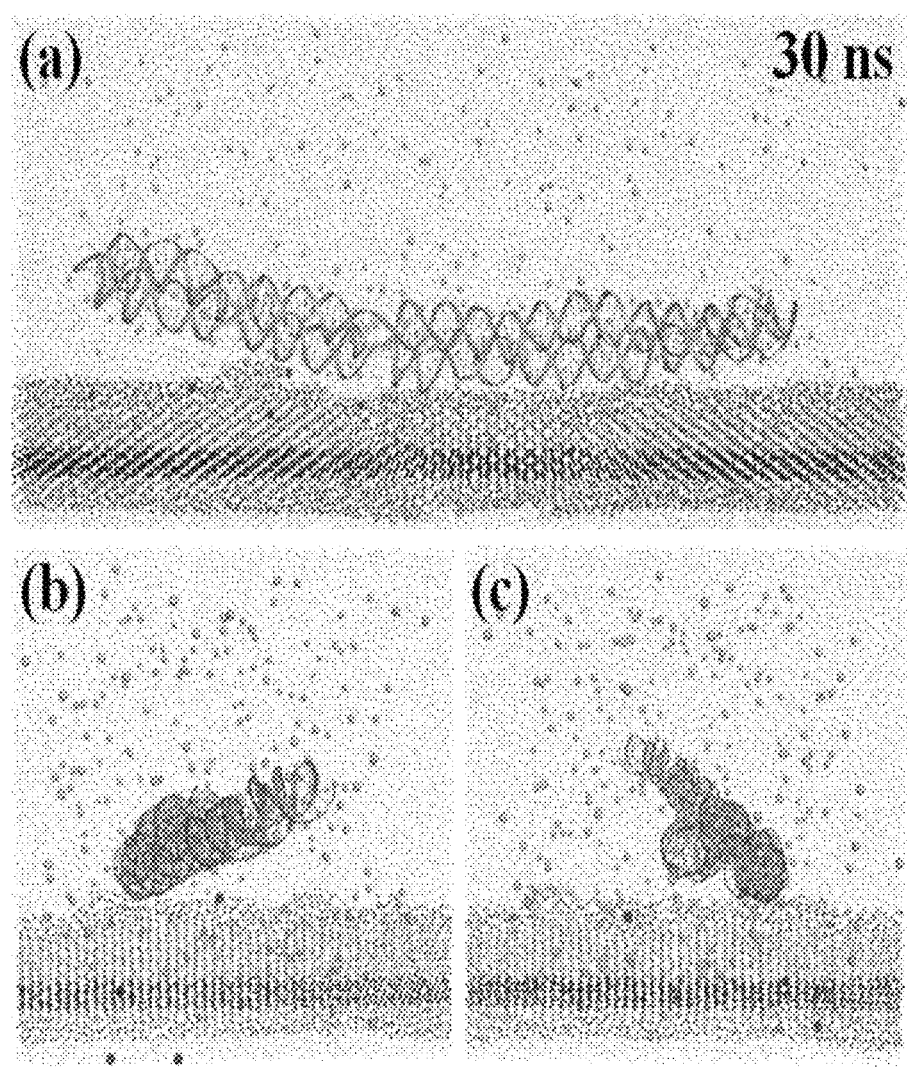

[FIG. 20]
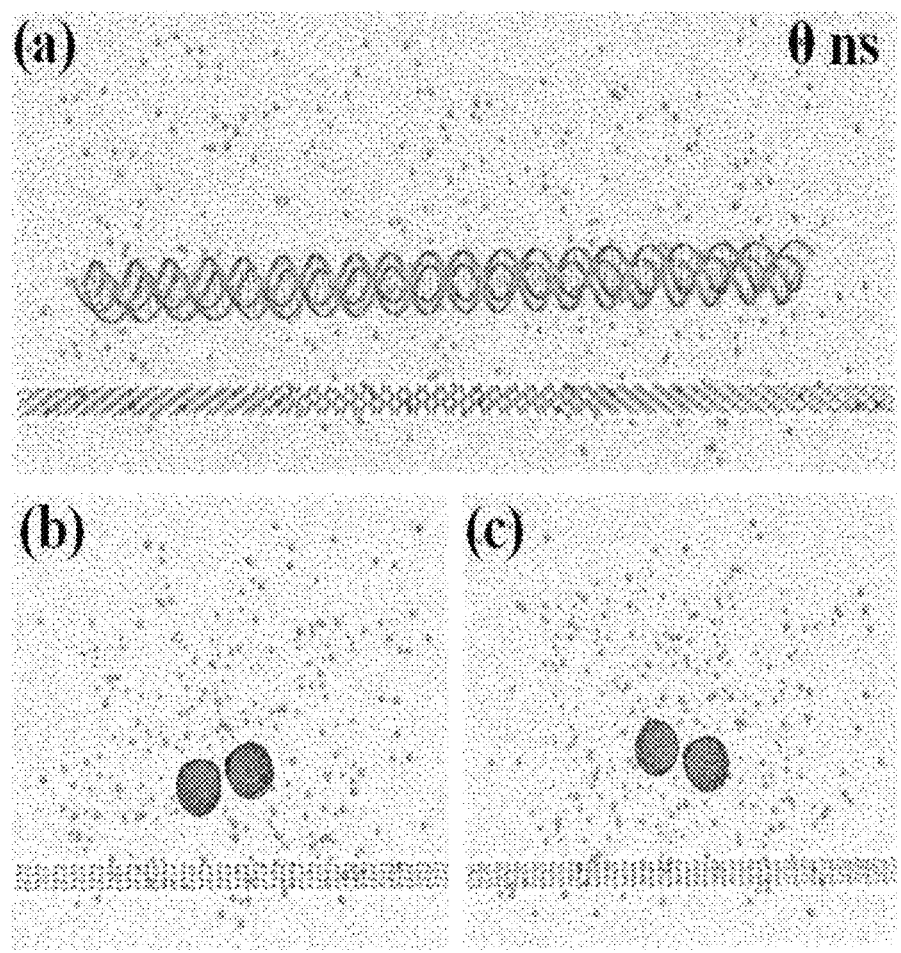

[FIG. 21]
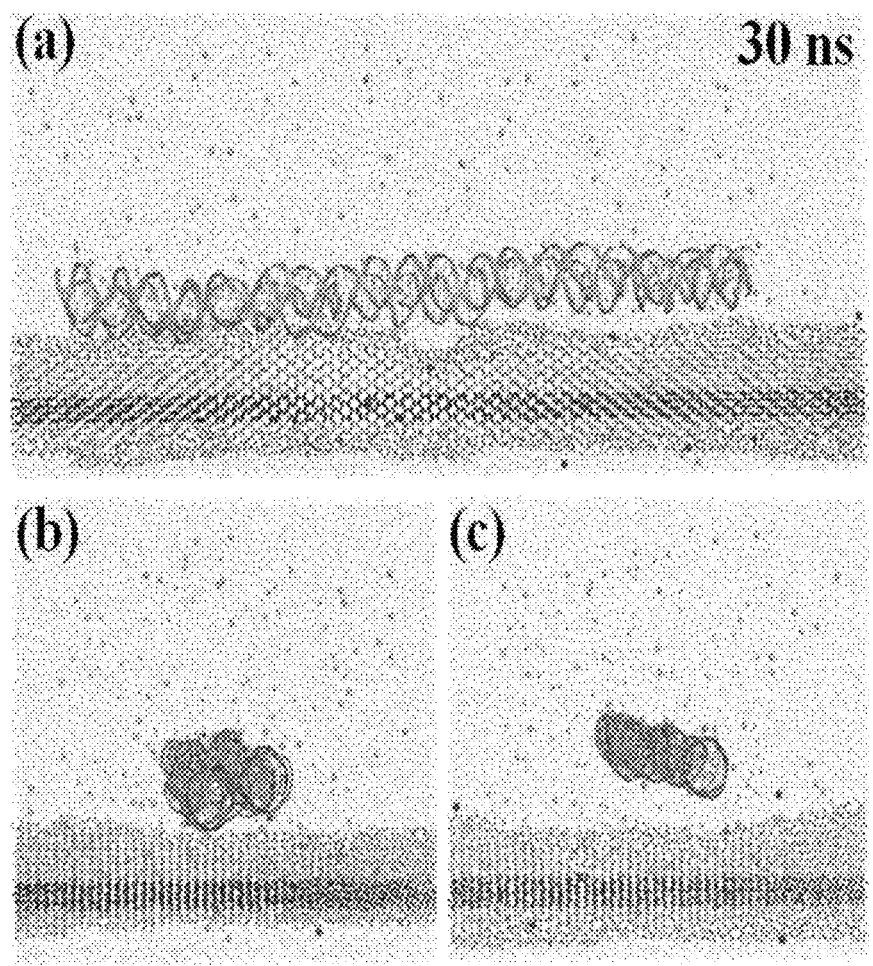

[FIG. 22]
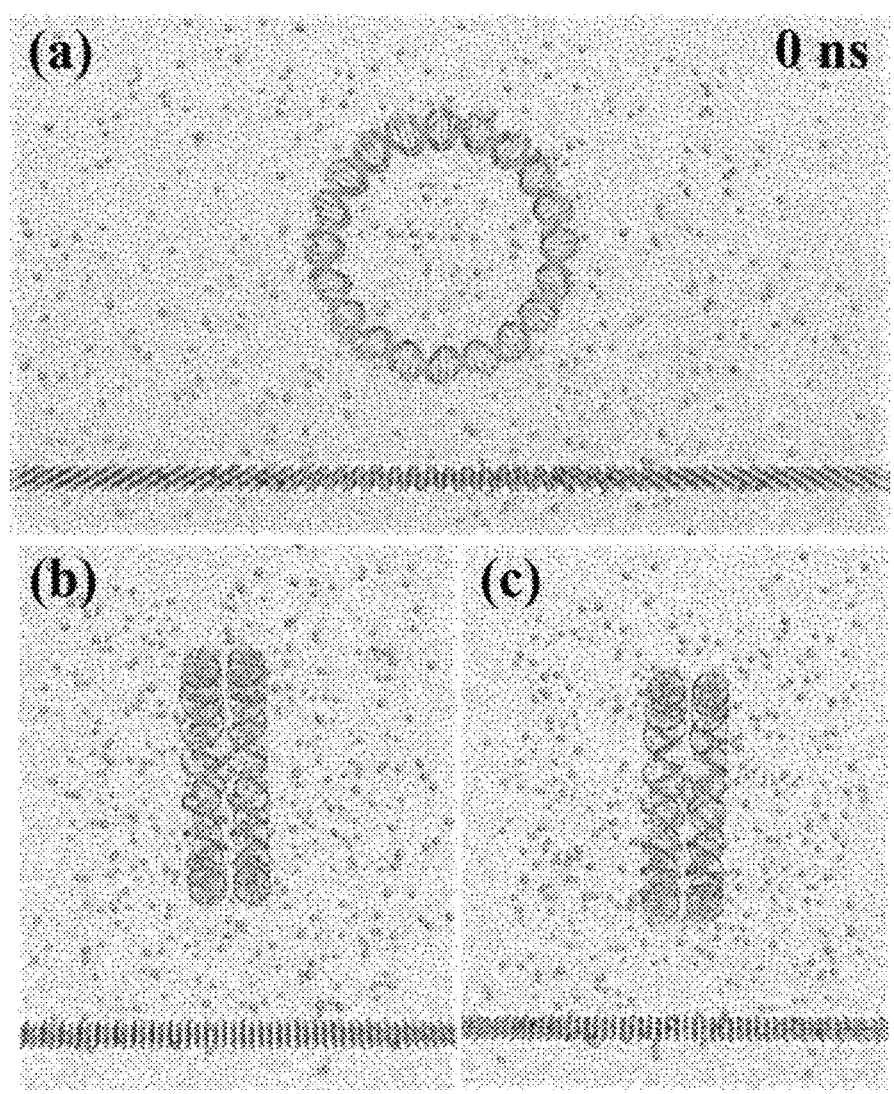

[FIG. 23]
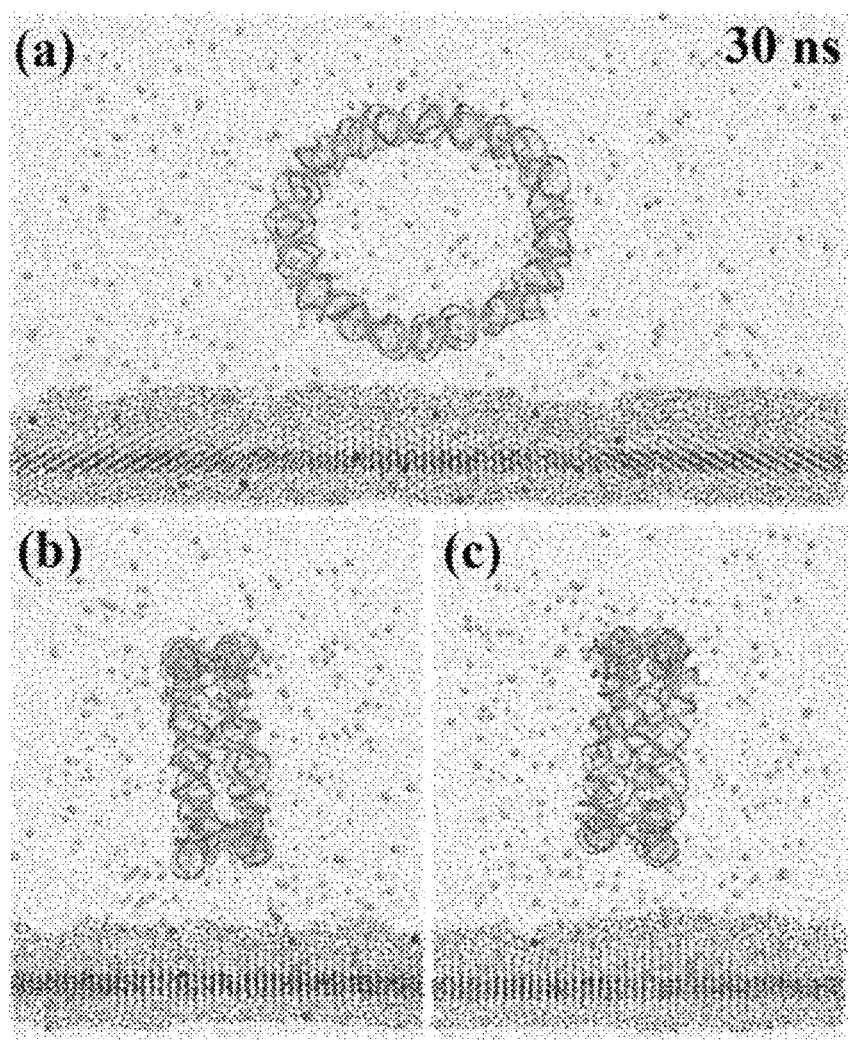

[FIG. 24]
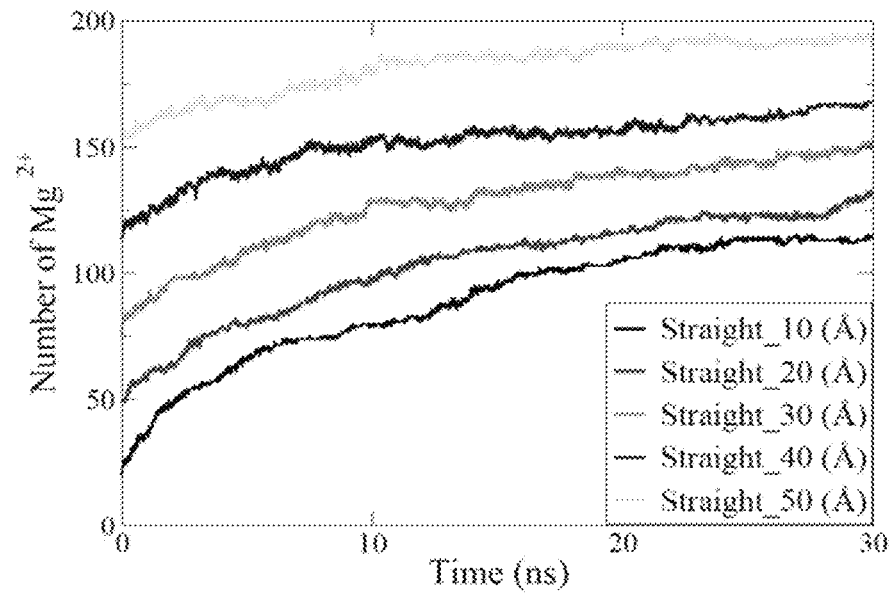
[FIG. 25]
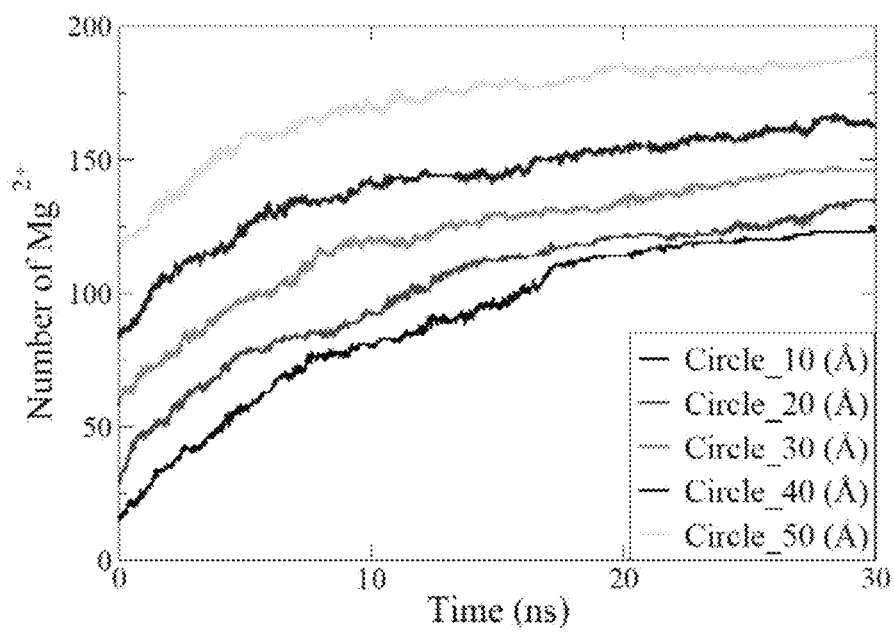

[FIG. 26]
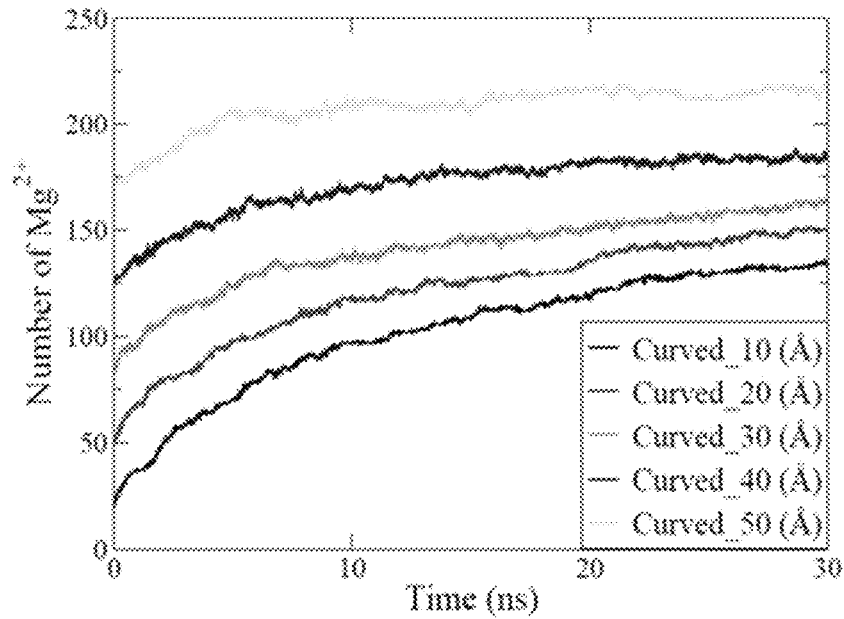
[FIG. 27]
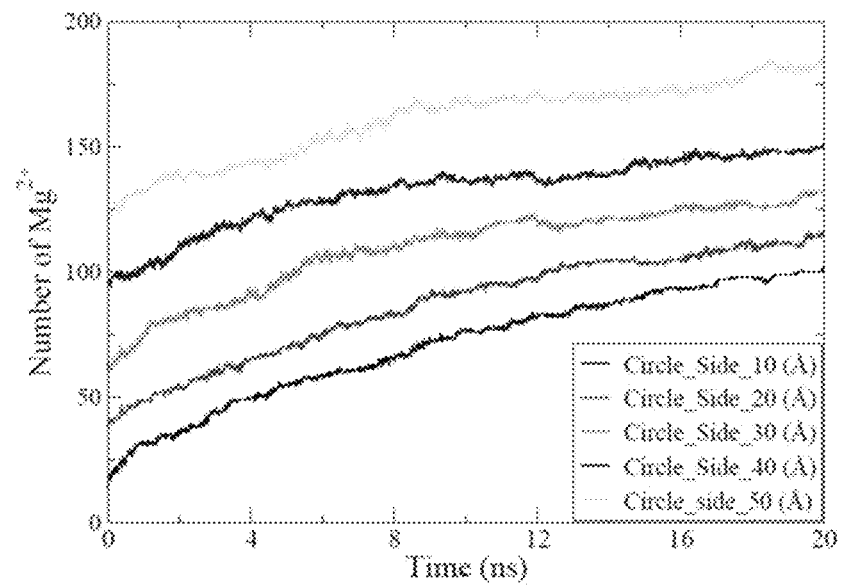

[FIG. 28]
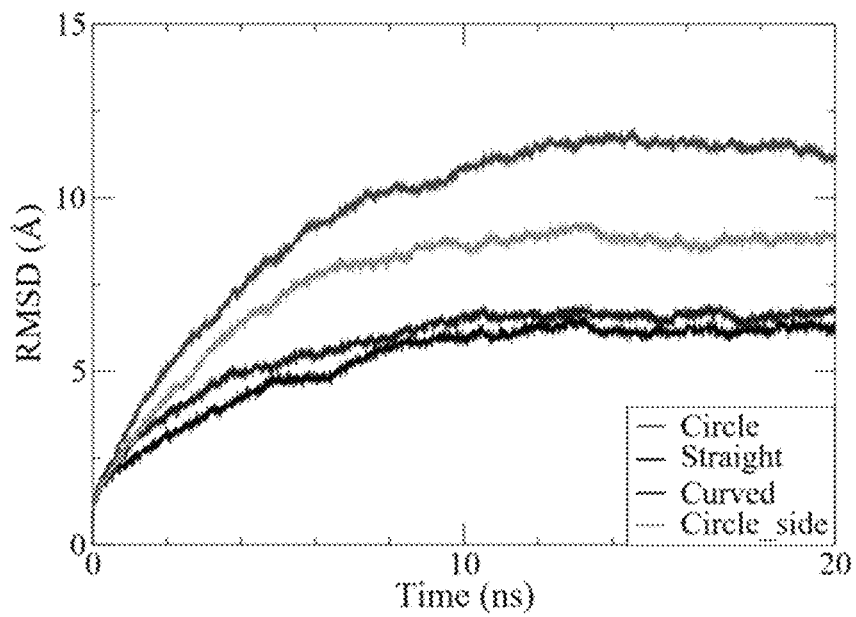
[FIG. 29]
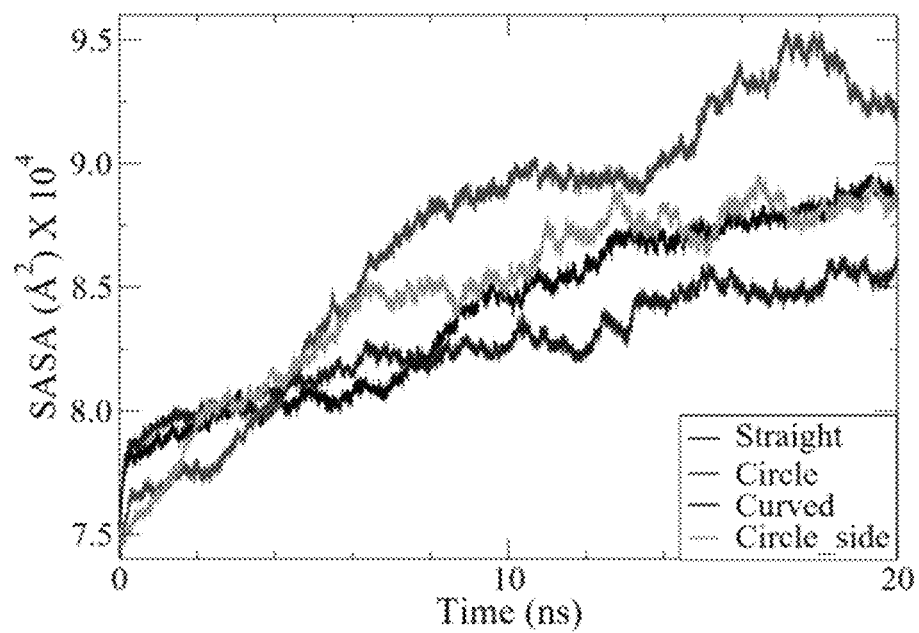

[FIG. 30]
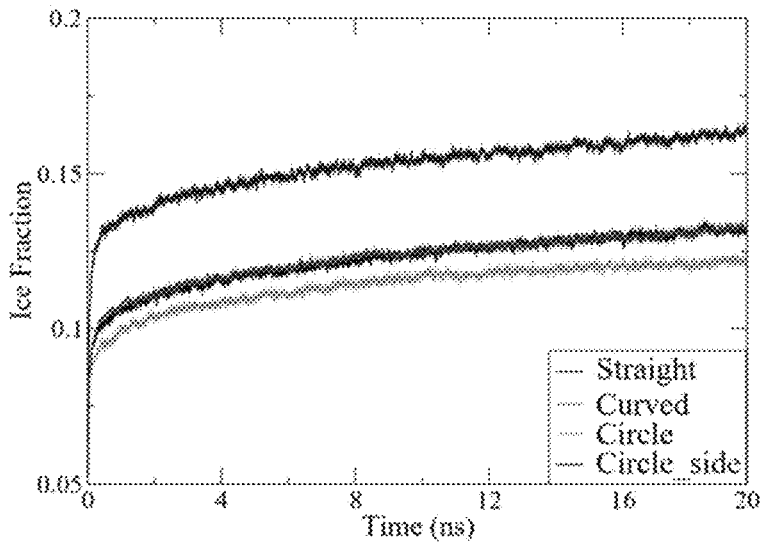
[FIG. 31]
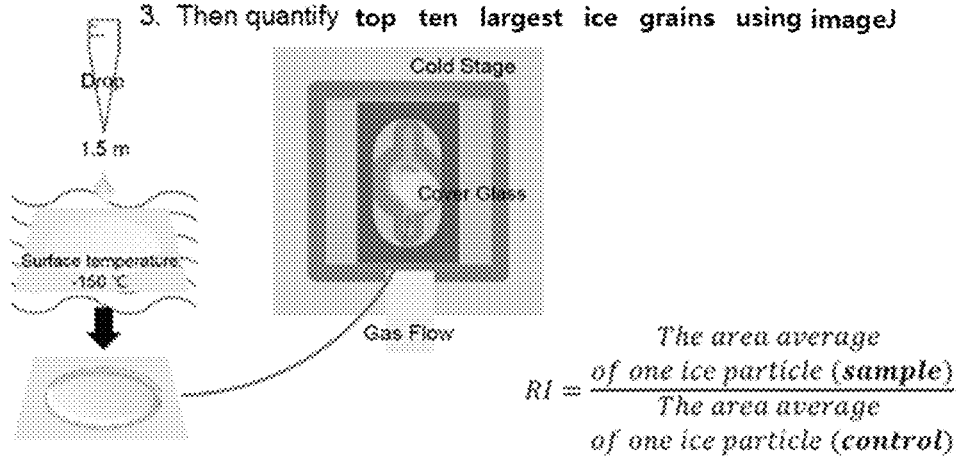
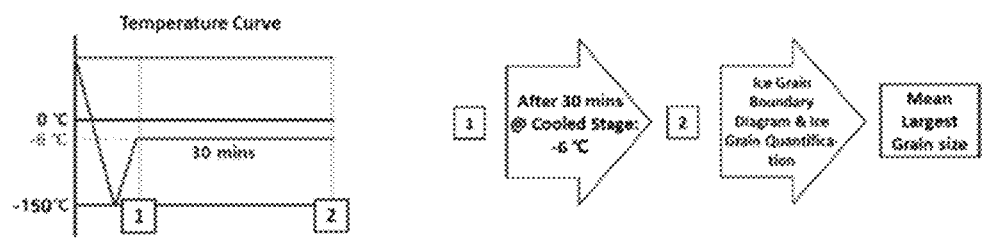

[FIG. 32]
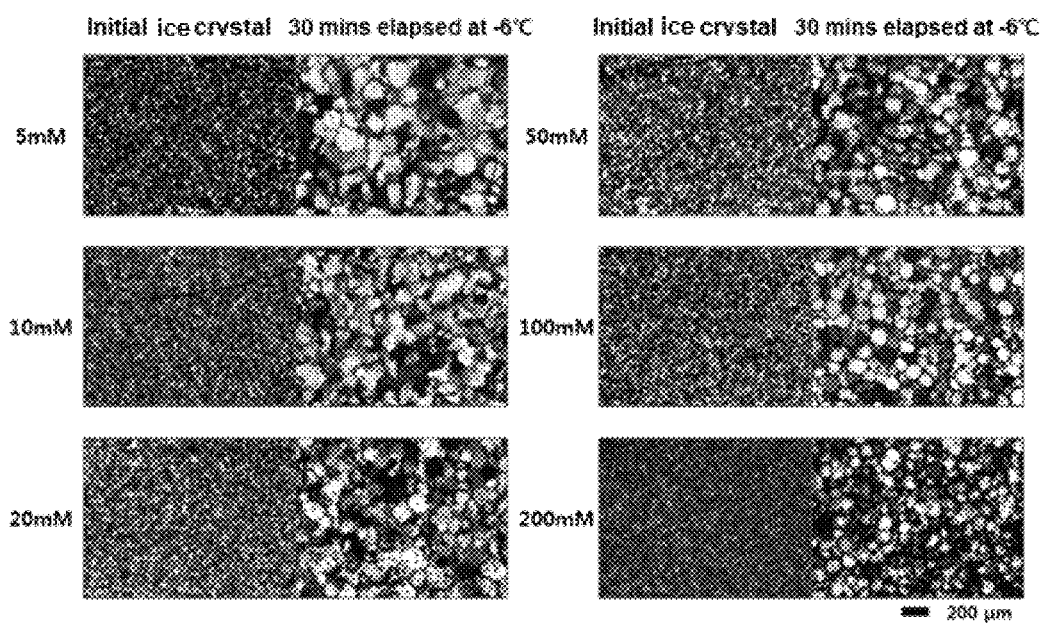

[FIG. 33]
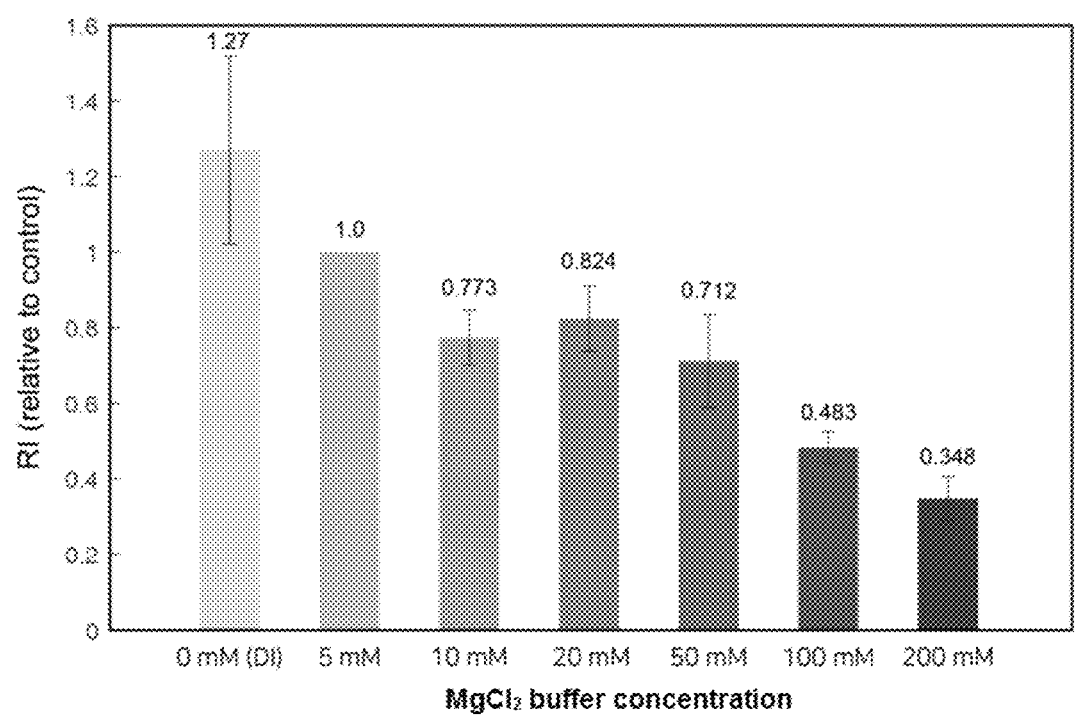

[FIG. 34]
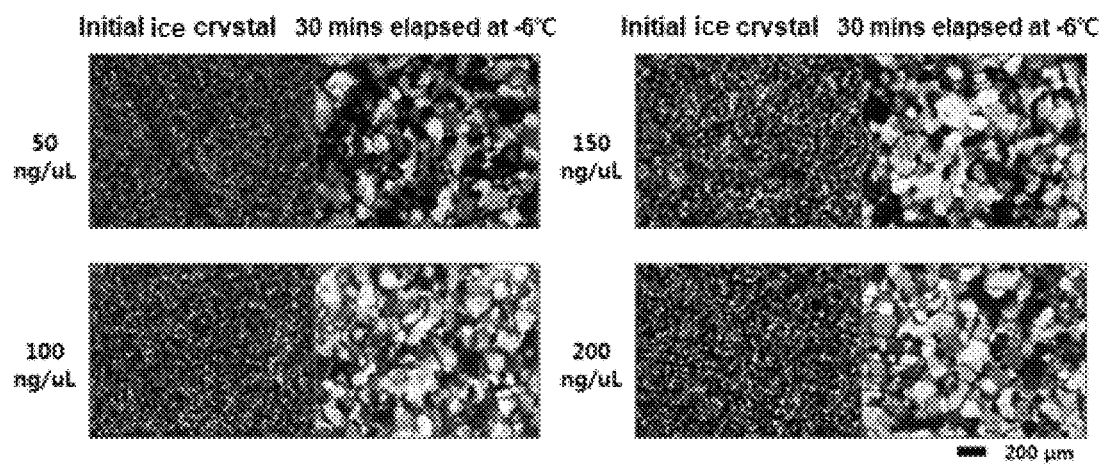
[FIG. 35]
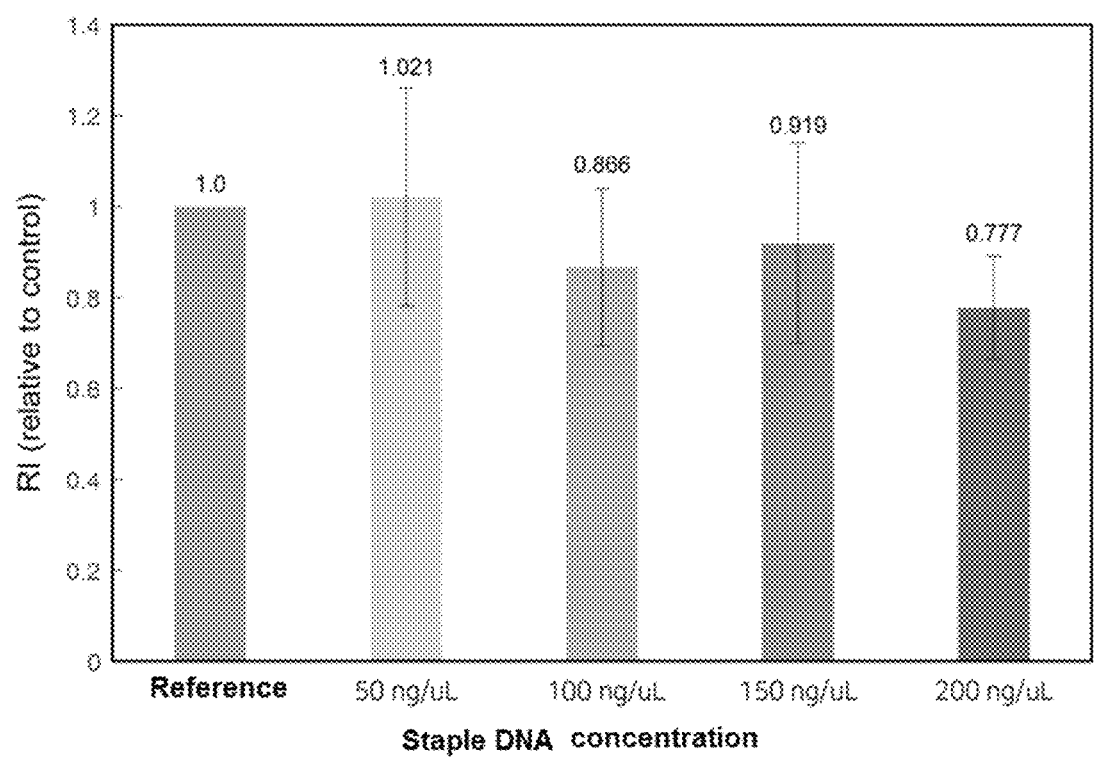

[FIG. 36]
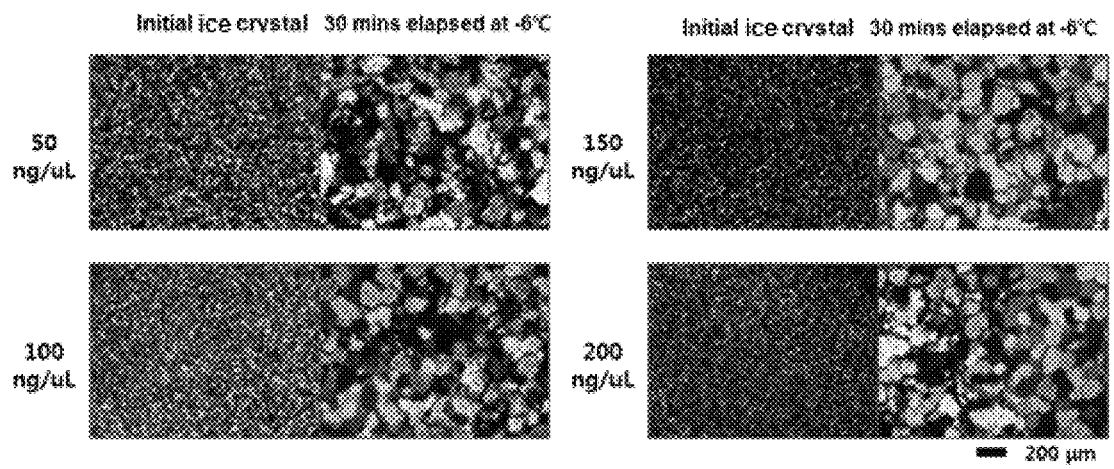
[FIG. 37]
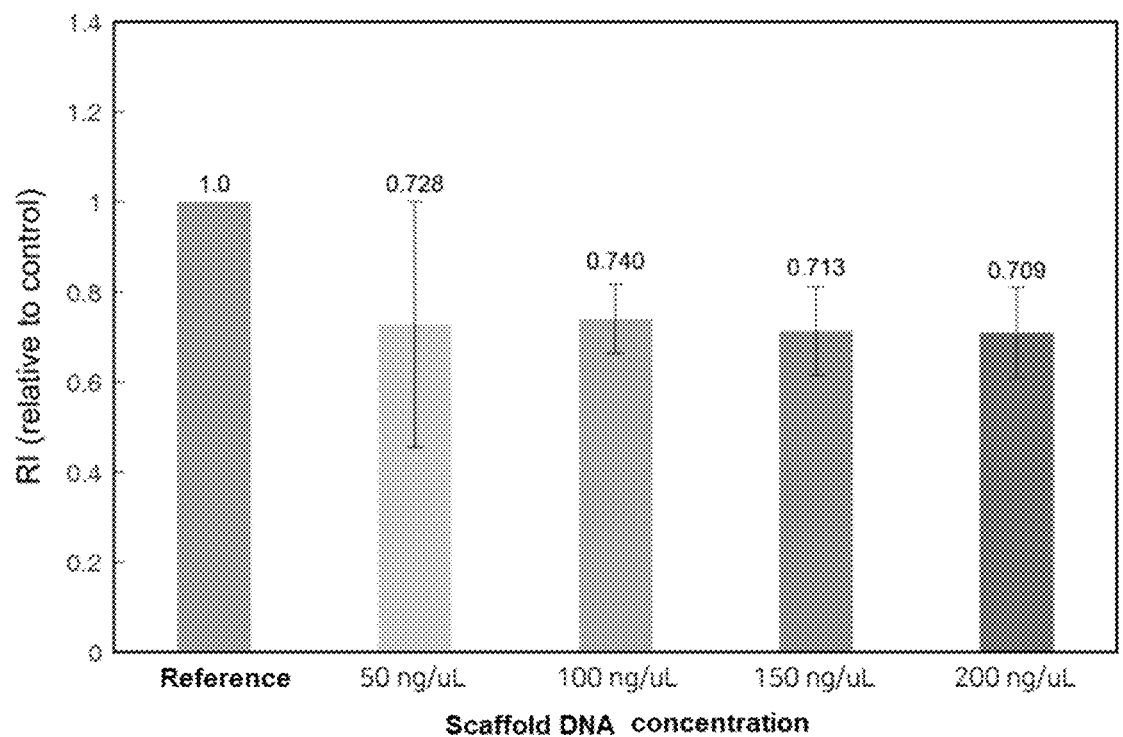

[FIG. 38]
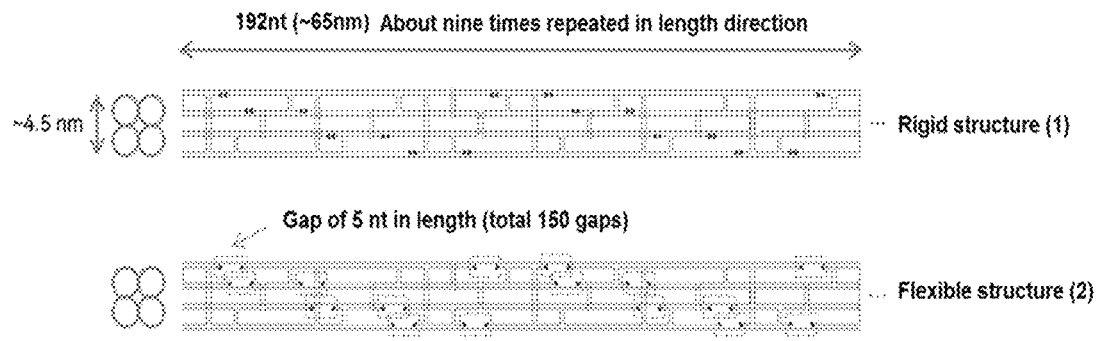
[FIG. 39]
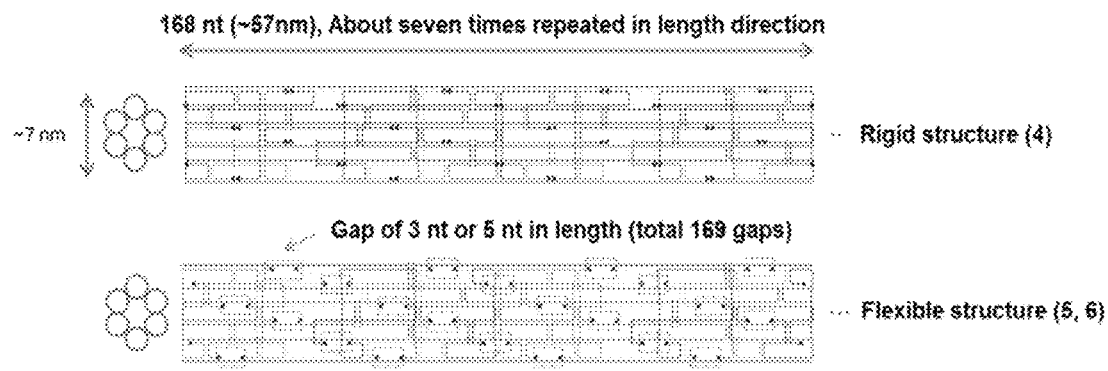
[FIG. 40]
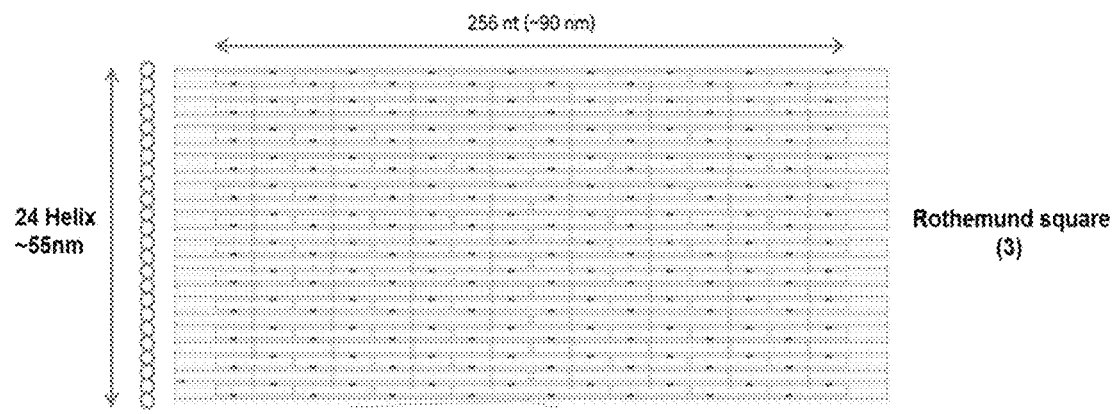

[FIG. 41]
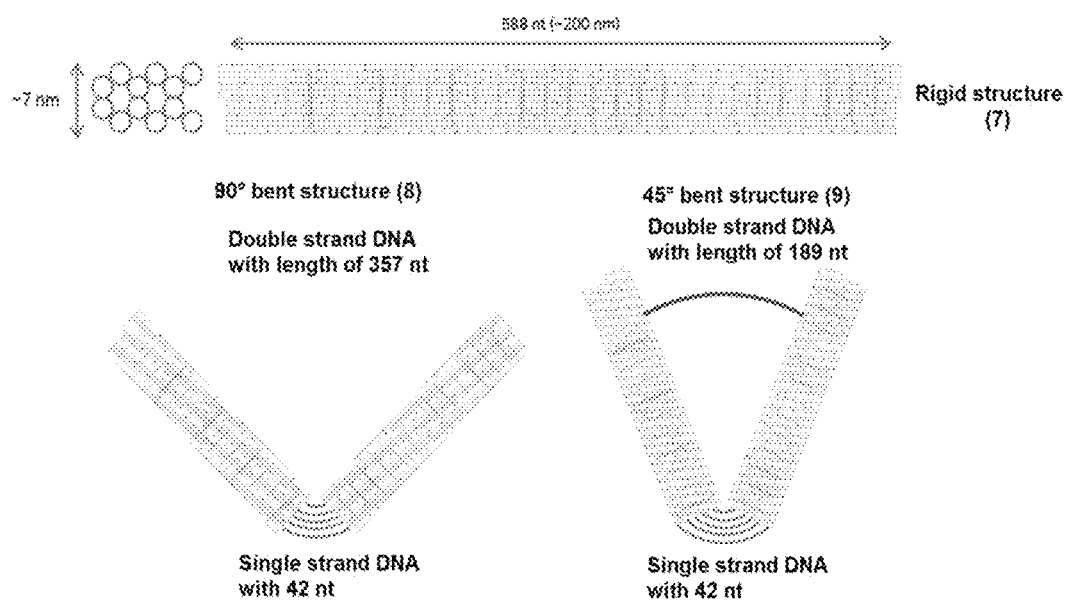
[FIG. 42]
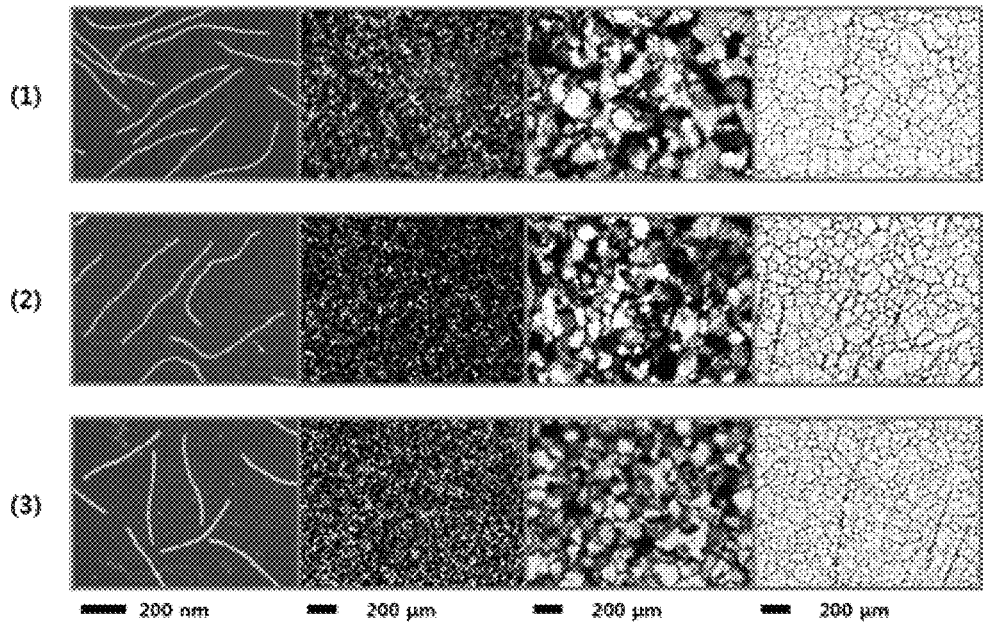

[FIG. 43]
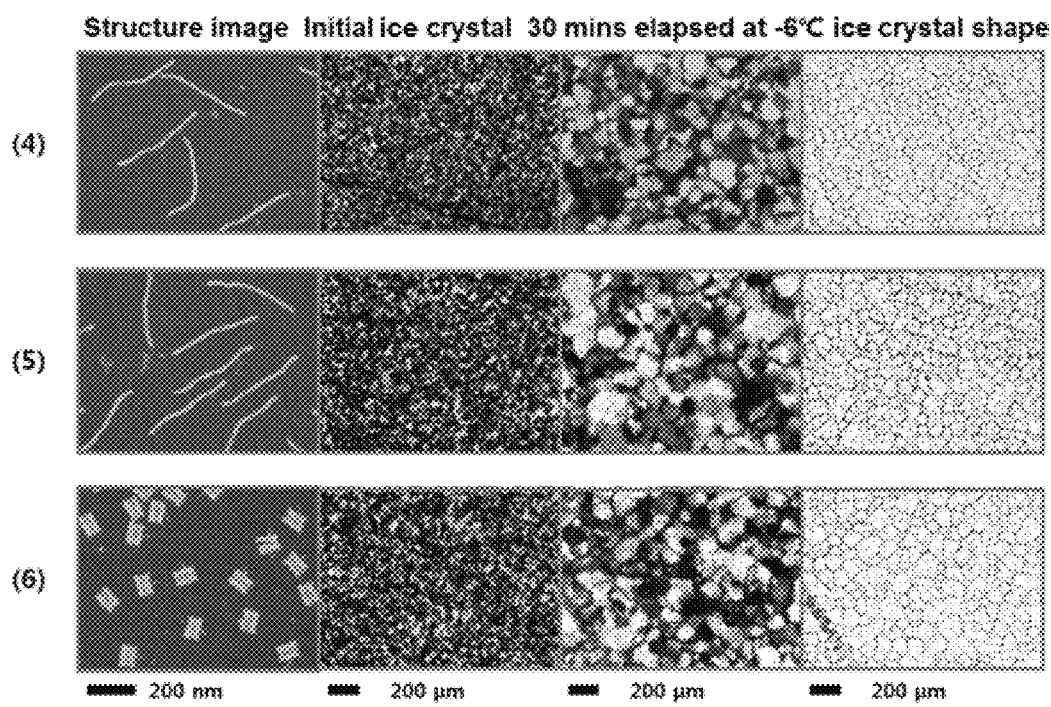
[FIG. 44]
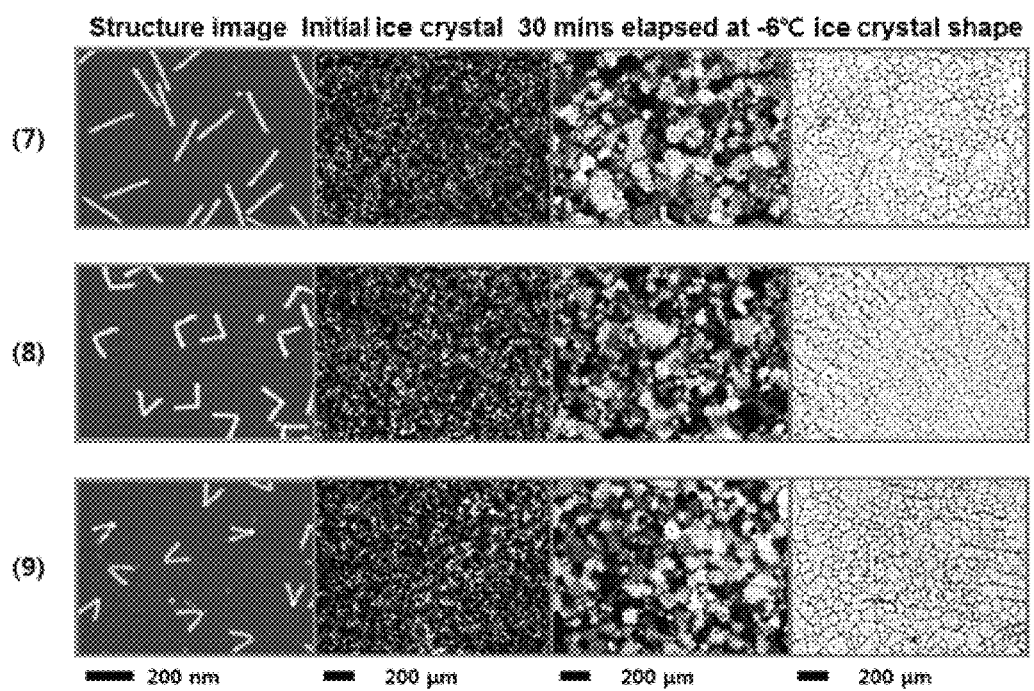

[FIG. 45]
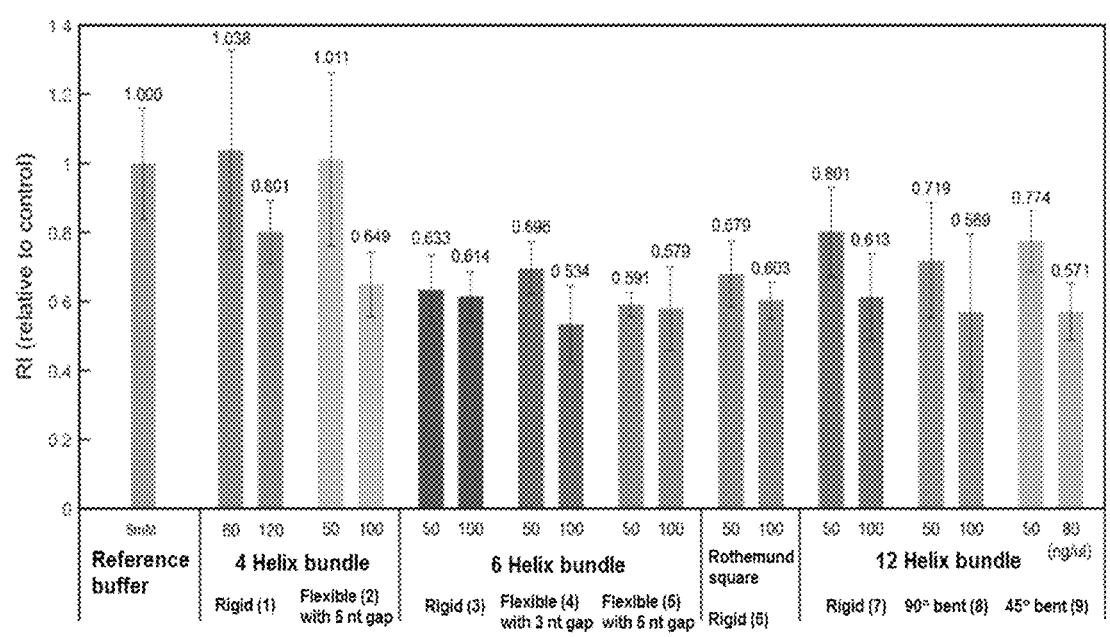

COMPOSITION FOR INHIBITING ICE RECRYSTALLIZATION

CROSS REFERENCE TO RELATED APPLICATIONS

The present application claims priority on Korean Patent Application No. 10-2019-0159420 filed on Dec. 3, 2019, the entire contents of which are incorporated by reference.

BACKGROUND OF THE INVENTION

1. Field of the Invention

The present invention relates to a composition for inhibiting ice recrystallization (i.e., ice crystal formation or growth).

2. Description of the Related Art

A cryoprotective agent (CPA) is a compound capable of reducing or inhibiting ice crystal formation in a solution exposed to a temperature below zero (0)° C. when present in the solution. Current CPA includes small molecules (often referred to as permeable CPAs), synthetic polymers, and cryoprotective proteins.

Currently, organ transplantation is the best treatment for end-stage organ failure in terms of a survival rate, quality of life, and cost effectiveness. Unfortunately, there is a steep gap between supply and demand of organ implants, which is one of important medical barriers that cause patients with debilitating diseases to experience low quality of life over a long period of waiting time. A marked lack of organs is due to significant amount of waste resulting from the absence of a reliable preservation method. Indeed, more than 50% of organs such as a lung, pancreas, and heart remain with being unharvested from the deceased donors.

In order to properly preserve the harvested organ, it is necessary to wash the organ with a cryopreservation liquid solution to remove blood, and stabilize the organ. Even after stabilizing the organ in the preservation solution, an available time for assignment, transport, and transplantation of the organ after removal from the donor is limited (about 6 to 12 hours). Due to such a small amount of time, most of the harvested organs will be distributed only to local patients. The reason is that it is not possible to identify the matching of organ in remote patients within a limited time. As a result of such a shortage, and although laws for prohibiting the sale of human organs are present in almost every country, illegal organ transactions and human trafficking have been increased to supply the demanded amount of the organs.

Current permeable CPAs used for long term storage generally include in particular ethylene glycol, 1,2-propanediol, dimethyl sulfoxide, formamide, glycerol, sucrose, lactose and D-mannitol. In order to reduce or inhibit ice crystal growth (hereinafter, 'ice recrystallization') at a temperature required for long term storage, an effective concentration of the permeable CPAs should be very high (60% or more thereof is often required). At such a high concentration, these compounds may be toxic to tissues that are trying to be preserved by the same, and mass removal of the CPAs upon warming prior to the transplantation may result in irreversible cell death.

Other CPAs used to reduce or inhibit ice crystal formation include synthetic polymers and cryoprotective proteins. Similar to the permeable CPA, each of them has their own drawbacks. For example, the synthetic polymer cannot penetrate a cell membrane. Thus, synthetic polymer CPA can only serve to control extracellular ice formation. In order to effectively preserve biological samples, ice crystal formation should be controlled both inside and outside the cell. Naturally-occurring cryoprotective proteins such as proteins isolated from fishes, plants, or insects, for example, are highly effective in preventing ice formation, but currently available cryoprotective proteins are extremely expensive as well as have a low purity. Additionally, the use of cryoprotective proteins for preserving the biological samples leads to an introduction of a potential supply source of immunogenicity.

DNA origami technology is a technique for preparing a desired structure by folding a long DNA strand typically having 7,000 to 8,000 bases into tens to hundreds of short DNA strands and immobilizing the same.

In DNA nanotechnology, DNA strands of specific pre-programmed sequences are synthesized using the Watson-Crick bonding law to prepare a structure having a desired shape. The DNA self-assembles with other DNAs having a complementary sequence thereto to form a double-stranded DNA. Using the same principle, two double-stranded DNAs can be linked in parallel through a junction portion (folded portion) called a Holliday Junction. When linking a plurality of double-stranded DNAs in this way, it is possible to produce a DNA nanostructure having a specific shape on a two-dimensional plane, and when extending the same principle onto a space, a three-dimensional structure having a specific lattice structure is prepared.

In the DNA origami, a long single-stranded DNA consisting of about 7,000 to 8,000 bases is used as a basic skeleton for preparing a structure, which is called a scaffold. In addition, about 200 short single-stranded DNAs consisting of about 20 to 50 bases are chemically synthesized and used by linking specific portions of the scaffold to prepare nanostructures. These DNAs are called staples. The number of staples and base sequences thereof should be precisely designed so that the staples can be bound only to the specific portions of the scaffold depending on a shape of the structure to be prepared.

Linking between the scaffold and staples is performed in an aqueous solution phase, and salt ions ($MgCl_2$ or NaCl) are added thereto to relax an electrostatic repulsion between a buffer as a buffer solution and the DNAs. Using a thermal annealing technique in which a solution containing all reactants is heated to a temperature of about 80° C., and then the temperature is slowly lowered for several hours to several tens of hours, the staples in the aqueous solution complementarily bind to the specified positions of the scaffold, thus to form DNA nanostructures.

Such a DNA origami technology allows to produce two/three-dimensional nanostructures having a complex shape with a high precision within several nanometers (nm), which cannot be prepared by a conventional top-down fabrication technique.

However, the correlation between these DNA structures and ice recrystallization is not known in the art.

PRIOR ART DOCUMENT

Patent Document

Korean Patent Laid-Open Publication No. 2018-0084782

SUMMARY OF THE INVENTION

An object of the present invention is to provide a novel composition for inhibiting ice recrystallization.

In addition, another object of the present invention is to provide a composition for freezing a cell or tissue.

Further, another object of the present invention is to provide a composition for freezing a food.

Furthermore, another object of the present invention to provide a method for freezing a cell or tissue.

To achieve the above objects, the following technical solutions are adopted in the present invention.

1. A composition for inhibiting ice recrystallization, including: a nucleic acid structure comprising a scaffold nucleic acid folded at predetermined positions to form a plurality of strands, and a plurality of staple nucleic acids, wherein at least a portion thereof has a complementary sequence to at least a portion of the scaffold nucleic acid, thereby binding to the scaffold nucleic acid to form a double strand.

2. The composition according to the above 1, wherein the nucleic acid structure includes a cation bound to at least a portion of negative charges thereof.

3. The composition according to the above 2 wherein the cation bound to the nucleic acid structure is $Na^+$, $NH_4^+$, or $Mg^{2+}$.

4. The composition according to the above 1, wherein the nucleic acid structure includes a surface which includes at least two helix bundles and is configured to come into contact with ice crystals.

5. The composition according to the above 1, wherein at least one of the helices of the nucleic acid structure has a gap which is formed in at least a portion thereof with a single strand.

6. The composition according to the above 1, wherein the nucleic acid structure has a twisted or curved helix bundle.

7. A composition for freezing a cell or tissue including the composition according to any one of the above 1 to 6.

8. A composition for freezing a food including the composition according to any one of the above 1 to 6.

9. A method for freezing a cell or tissue including exposing a cell or tissue of a subject to a temperature below zero in the presence of the composition according to the above 7.

The composition of the present invention has an excellent effect of inhibiting ice recrystallization, thereby, it is possible to increase a survival rate of cells due to having the above-described effect upon cryopreservation of the cells, and maintain a texture of food even when using the composition in the freezing of food.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a diagram illustrating a case in which a scaffold nucleic acid and staple nucleic acids bind to each other to form a structure;

FIG. 2 is diagrams illustrating several nucleic acid origami structures, wherein A is 4 helix bundle (rigid structure), B is 4 helix bundle (flexible structure), C is Rothemund square, D is 12 helix bundle (rigid structure), E is 12 helix bundle (90° bent structure), and F is 12 helix bundle (45° bent structure);

FIG. 3 is a diagram illustrating 4, 6 and 12 helix bundle (HB)-rigid structures;

FIG. 4 is a diagram illustrating 4 helix bundle flexible structure, and 6 helix bundle flexible structure;

FIG. 5 is a diagram illustrating origami structures with or without a gap;

FIG. 6 is a diagram illustrating an octahedral structure of water molecules surrounding a cation in a primary shell;

FIG. 7 is a diagram illustrating a secondary shell structure of the cation;

FIG. 8 is graphs illustrating ice fraction results according to various ion concentrations at 225 K. Wherein, (A) is a graph illustrating ice fractions of 10 mM of NaCl and 10 mM $MgCl_2$ solutions with respect to a control (with no ion+pure water), which are shown in colors of $MgCl_2$ (Pink), NaCl (Brown), and control (Green); (B) is a graph illustrating ice fractions of 50 mM of NaCl and 50 mM $MgCl_2$ solutions with respect to the control (with no ion+pure water), which are shown in colors of $MgCl_2$ (Blue), NaCl (Cyan), and control (Green); (C) is a graph illustrating ice fractions of 150 mM of NaCl and 150 mM $MgCl_2$ solutions with respect to the control (with no ion+pure water), which are shown in colors of $MgCl_2$ (Red), NaCl (Orange), and control (Green); and (D) is a graph collectively illustrating (A), (B) and (C);

FIG. 9 is a graph illustrating radical distribution functions of $Mg^{2+}$ ions and water molecules;

FIG. 10 is a diagram illustrating dynamic equilibrated DNA structures at 0 ns and 40 ns;

FIG. 11 is a graph illustrating RMSD values of five DNA structures in the presence of 10 mM $MgCl_2$;

FIG. 12 is a graph illustrating SASA values of five DNA structures in the presence of 10 mM $MgCl_2$;

FIG. 13 is a graph illustrating the number of $Mg^{2+}$ ions within 10 Å of DNA backbone;

FIG. 14 is a diagram illustrating distributions of $Mg^{2+}$ ions within 10 Å of DNA backbone at 0 ns and 40 ns;

FIG. 15 is a graph illustrating ice fractions of several DNA origami structures;

FIG. 16 is diagrams illustrating an initial structure of a circular DNA origami structure at 0 ns, which includes an ice seed layer: prism surface (Blue) of 8 Å thickness, DNA backbone (Orange), and $Mg^{2+}$ ions (Green), wherein (a), (b) and (c) are side, front and rear views, respectively;

FIG. 17 is diagrams illustrating a dynamic structure of the circular DNA origami structure at 30 ns, which includes an ice seed layer: prism surface with a thickness of 8 Å (Blue), DNA backbone (Orange), $Mg^{2+}$ ions (Green), $Mg^{2+}$ ions (Red) on a clipped plane), and growing ice (Cyan), wherein (a), (b) and (c) are side, front and rear views, respectively;

FIG. 18 is diagrams illustrating an initial structure of a curved DNA origami structure at 0 ns, which includes an ice seed layer: prism surface with a thickness of 8 Å (Blue), DNA backbone (Orange), and $Mg^{2+}$ ions (Green), wherein (a), (b) and (c) are side, front and rear views, respectively;

FIG. 19 is diagrams illustrating a dynamic structure of the curved DNA origami structure at 30 ns, which includes an ice seed layer: prism surface with a thickness of 8 Å (Blue), DNA backbone (Orange), and $Mg^{2+}$ ions (Green), wherein (a), (b) and (c) are side, front and rear views, respectively;

FIG. 20 is diagrams illustrating an initial structure of a linear DNA origami structure at 0 ns, which includes an ice seed layer: prism surface with a thickness of 8 Å (Blue), DNA backbone (Orange), and $Mg^{2+}$ ions (Green), wherein (a), (b) and (c) are side, front and rear views, respectively;

FIG. 21 is diagrams illustrating a dynamic structure of the linear DNA origami structure at 30 ns, which includes an ice seed layer: prism surface with a thickness of 8 Å (Blue), DNA backbone (Orange), and $Mg^{2+}$ ions (Green), wherein (a), (b) and (c) are side, front and rear views, respectively;

FIG. 22 is diagrams illustrating an initial structure of the circular side DNA origami structure at 0 ns, which includes an ice seed layer: prism surface with a thickness of 8 Å

(Blue), DNA backbone (Orange), and $Mg^{2+}$ ions (Green), wherein (a), (b) and (c) are side, front and rear views, respectively;

FIG. 23 is diagrams illustrating the dynamic structure of the circular side DNA origami structure at 30 ns, which includes an ice seed layer: prism surface with a thickness of 8 Å (Blue), DNA backbone (Orange), and $Mg^{2+}$ ions (Green), wherein (a), (b) and (c) are side, front and rear views, respectively;

FIG. 24 is a graph illustrating the number of $Mg^{2+}$ ions around the linear DNA origami;

FIG. 25 is a graph illustrating the number of $Mg^{2+}$ ions around the circular DNA origami;

FIG. 26 is a graph illustrating the number of $Mg^{2+}$ ions around the bent DNA origami;

FIG. 27 is a graph illustrating the number of $Mg^{2+}$ ions around the circular side DNA origami;

FIG. 28 is a graph illustrating RMSD values for 20 ns of several DNA origamis;

FIG. 29 is a graph illustrating SASA values for 20 ns of several DNA origamis;

FIG. 30 is a graph illustrating ice fraction during 20 ns of several DNA origamis;

FIG. 31 is a schematic diagram illustrating a method for measuring recrystallization inhibition (RI) effects;

FIGS. 32 and 33 are photographs and a graph illustrating RI measurement results for a buffer solution containing only $MgCl_2$ in pure distilled water;

FIGS. 34 and 35 are photographs and a graph illustrating RI measurement results for a solution in which unstructured single-stranded DNA strands are present;

FIGS. 36 and 37 are photographs and a graph illustrating RI measurement results of a scaffold DNA sample;

FIG. 38 is a diagram illustrating 4 helix bundle rigid structure and flexible structure;

FIG. 39 is a diagram illustrating 6 helix bundle rigid structure and flexible structure;

FIG. 40 is a diagram illustrating a Rothemund square structure;

FIG. 41 is a diagram illustrating 12 helix bundle firm structure and bent structures; and FIGS. 42 to 45 are photographs and a graph illustrating RI effects of DNA origami structures.

DETAILED DESCRIPTION OF THE INVENTION

Hereinafter, the present invention will be described in detail.

The present invention provides a composition for inhibiting ice recrystallization.

The composition for inhibiting ice recrystallization may inhibit ice crystal formation or growth, that is, ice recrystallization.

Ice crystals can grow through ice recrystallization, which refers to a process of growing from small ice crystals to larger ice crystals, and the growth thereof occurs according to Ostwald ripening mechanism. The Ostwald ripening may be performed in a dissolution-diffusion-refreezing or a sublimation-diffusion-condensation mechanism. In other words, the growth of two adhered ice crystals does not occur simultaneously, but rather as small ice crystals are melted between the crystals, and spread toward large ice crystals, thus to be a part of large ice crystals while refreezing.

Antifreezing refers to actions of preventing ice formation or lowering a speed of ice formation, preventing ice recrystallization or lowering a speed of ice recrystallization, or maintaining a size of ice crystals to be small.

The composition for inhibiting ice recrystallization of the present invention includes a nucleic acid structure.

The nucleic acid structure may be a nucleic acid origami (DNA origami in FIG. 1) structure.

The nucleic acid may be DNA or RNA.

The nucleic acid origami structure is a structure formed by folding predetermined portions of a scaffold nucleic acid (DNA scaffold in FIG. 1) while binding to a plurality of staple nucleic acids, as shown in FIG. 1.

The scaffold nucleic acid is a single-stranded nucleic acid, of which length may be appropriately selected depending on a length, size, shape, and the like of the structure to be formed, and a type of nucleic acid strand having a length of about 7000 to 8000 nucleotides (nt) may be used. In a specific embodiment of the present invention, M13mp18 DNA having a length of 7,249 nt was used, but it is not limited thereto. When preparing the DNA structure using M13mp18 scaffold DNA, the molecular weight of the resulting structure is about 5 megadaltons, which corresponds to about $10^{-20}$ kg, but it is not limited thereto.

In the staple nucleic acids, at least a portion thereof has a complementary sequence to at least a portion of the scaffold nucleic acid, thereby binding to the scaffold nucleic acid to form a double strand, and allowing the scaffold nucleic acid to be folded or immobilized at specific positions.

The length of the staple nucleic acid may be appropriately selected depending on the length, size, shape, and the like of the structure to be formed, for example, may be 20 to 50 nt, but it is not limited thereto.

The nucleic acid origami structure is a specific structure formed by binding the staple nucleic acids to specific positions of the scaffold nucleic acid and folding the staple nucleic acids at the specific positions, and the staple nucleic acids are designed so that the scaffold nucleic acid has such a specific structure.

The design of the staple nucleic acid may be performed according to a conventional method, and for example, a design program such as caDNAno may be used, but it is not limited thereto.

The nucleic acid origami structure may be prepared using conventional thermal annealing techniques.

This technique starts by heating the scaffold nucleic acid and staple nucleic acids as raw materials to a high temperature (for example, 70 to 100° C.), so that all nucleic acid strands are in a single-stranded state. The nucleic acid strand has a melting temperature according to a base sequence thereof, and in a case of above the melting temperature, the nucleic acid exists mainly as a single strand, and in a case of below the melting temperature, the nucleic acid exists mainly as a double strand. When slowly lowering the temperature of the reaction solution, the nucleic acid strands start to exist as the double strand while complementarily binding, and in the nucleic acid origami, about 200 staple nucleic acids bind to the designed positions while cooperatively binding, thereby creating a structure having a desired shape.

Since the respective staple nucleic acids have different base sequences, times of binding are slightly different from each other. However, because the conventional thermal annealing technique allows the temperature to be gradually lowered over a sufficient time (more than several hours), a condition, in which all the staple nucleic acids are sufficient to bind, is formed, and therefore, it is possible to prepare a structure so as to have the desired shape regardless of the base sequences.

The scaffold nucleic acid is folded at the predetermined positions to form a plurality of strands, and the staple nucleic acids have sequences designed so as to allow the scaffold nucleic acid to be folded at the predetermined positions. Therefore, the scaffold nucleic acid forms a predetermined structure while the staple nucleic acids bind to the scaffold nucleic acid by the above method.

The scaffold nucleic acid strands and the staple nucleic acids may bind to each other to form double strands (double helices), wherein the nucleic acid origami structure may have, for example 2 to 50, 2 to 45, 2 to 40, 2 to 35, 2 to 30, 2 to 25, 2 to 20, 2 to 12, or 4 to 12 helix bundles, and specifically may have 4 to 12 helix bundles, but it is not limited thereto. FIGS. 2 and 4 illustrate nucleic acid origami structures having various numbers of helix bundles.

The nucleic acid origami structure may have a gap between opposite ends of at least some adjacent staple nucleic acids.

As shown on the right side in FIG. 5, the gap refers to a single-stranded region formed between opposite ends of adjacent staple nucleic acids, may mean a scaffold nucleic acid single-stranded region that does not complementary bind to the staple nucleic acid, and specific schemes may be confirmed in FIGS. 4, 5 and the like.

As the scaffold nucleic acid does not complementary bind to the staple nucleic acid due to the gap thus not to form a double helix structure, a target site including the gap results in a weak rigidity. Therefore, macroscopically, it is possible to control the rigidity of the entire nucleic acid origami structure in a direction of being decreased using the gap.

The length of the gap may be represented by the number of nucleotide bases in the single-stranded region, and the gap may be formed in a length of 1 to 20, 1 to 19, 1 to 18, 1 to 17, 1 to 16, 1 to 15, 1 to 14, 1 to 1 13, 1 to 12, 1 to 11, 1 to 10, 1 to 9, 1 to 8, 1 to 7, 1 to 6, 1 to 5 nucleotides, more specifically 1 to 10 nucleotides. However, in an aspect of maintaining the shape of the entire nucleic acid origami structure by maintaining a gap having an appropriate length, and considering integrity in self-assembly process, the gap is preferably formed in a length of 1 to 5 nucleotides.

The number of gaps refers to the number of single-stranded regions in the target site for controlling the rigidity, and by setting (the number of staple nucleic acids—2) to be the maximum number of gaps, it is possible to control the rigidities of the target site including the gaps and the entire nucleic acid origami structure.

The gap may be formed so as to be a gap having a length of 10 nucleotides or more, 9 nucleotides or more, 8 nucleotides or more, 7 nucleotides or more, 6 nucleotides or more, 5 nucleotides or more, 4 nucleotides, or 3 nucleotides or more with a Holliday Junction. In an aspect of forming a nucleic acid origami structure through a complete self-assembly process between the scaffold nucleic acid and the staple nucleic acid, it may be formed so as to be a gap having a length of 3 nucleotides or more.

The formation of the nucleic acid origami structure may be carried out in the presence of a cation in order to reduce a repulsive force between the negative charges of phosphate groups of the nucleic acid backbone. Accordingly, the nucleic acid origami structure may further include a cation bound to negative charges thereof.

The cation is a monovalent or divalent cation, and may be, for example, $Na^+$, $Mg^{2+}$, $NH_4^+$, and the like, but it is not limited thereto.

It is determined that water molecules are bound to the cations in the nucleic acid origami structure, thereby preventing them from being used for ice recrystallization. Specifically, FIGS. 6 and 7 illustrate arrangements of water molecules around $Mg^{2+}$ ion. The inventors of the present invention have found that six water molecules (a first shell) initially bound to the $Mg^{2+}$ ion are not easily replaced with other surrounding water molecules, thereby maintaining an octahedron structure during molecular dynamics (MD) simulation. In addition, from a more detailed analysis of water molecules around the $Mg^{2+}$ ion, it was found that 12 water molecules are also bound to a second shell. It is expected that, although binding is not as rigid as that of the first shell, these water molecules present in the second shell are used for ice recrystallization, but play a role of delaying ice recrystallization by decreasing a growth rate of ice crystals. The six water molecules indicated in green are water molecules having the Octahedron structure bound to the first shell, and the remaining water molecules are twelve water molecules around the $Mg^{2+}$ ion bound to the second shell. The ion indicated in blue is the $Mg^{2+}$ ion. The water molecules around the $Mg^{2+}$ ion exist within an $Mg^{2+}$ potential, and thus, it can be seen that, in participating in the surrounding ice recrystallization, it is different from the ice recrystallization of a solution containing only pure water molecules. This is believed to be the cause of ice recrystallization inhibition by the $Mg^{2+}$ at the molecular level.

Of course, even if the nucleic acid strands do not form a structure, the concentration of surrounding $Mg^{2+}$ ion may be partially increased due to the negative charges of the nucleic acid backbone. But, if the nucleic acids are not densely concentrated with a constant shape and rigidity, the water molecules bound to $Mg^{2+}$ ion cannot be constantly held during growing the ice crystals, such that it seems difficult to exhibit RI effects.

The nucleic acid origami structure may have a structure so that a large amount of cations are distributed on the ice surface during growing the ice crystals.

In this regard, the nucleic acid origami structure according to the present invention may include a twisted or curved helix bundle.

For example, a direction in which the helix bundle is twisted may be controlled by an insertion or deletion of a base, and the bundle may be twisted in a right direction by inserting the base into the helix or may be twisted in a left direction by deleting the base. A degree of twisting may be controlled by the number of bases. The number of bases to be inserted or deleted may be one or two per every length of 21 bases in which the helix is rotated twice, and even if the number of bases exceeds the above range, there is no particular limitation as long as there is no problem in maintaining the structure.

Further, for example, the base is inserted into one helix of a plurality of helices, and the base is not be inserted into other helices or the base is deleted so as to make a difference in the length between the helices, so that the helix bundle may be curved.

In addition, the nucleic acid origami structure may include a surface that can come into contact with an ice recrystallization surface in an aspect of inhibiting ice crystal formation or growth, that is, ice recrystallization. It is also possible to maximize the ice recrystallization inhibition effect by coming into contact the surface of the nucleic acid origami structure with the ice recrystallization surface over a large area in a form of a plane rather than a line.

In addition, the present invention relates to a composition for freezing a cell or tissue.

When cryopreserving cells or tissues, cell membranes may be damaged due to ice recrystallization during melting the cryopreserved cells or tissues for subsequent use, thereby resulting in damaging the cells and tissues due to occurred cell dehydration. Organisms living in a lower-temperature environment may be more easily damaged by ice recrystallization.

The composition of the present invention may be applicable to all cells that are commonly used by freezing for preservation, and may include, for example, prokaryotic cells; eukaryotic cells; microorganisms; animal cells; cancer cells, sperms; eggs; stem cells including adult stem cells, embryonic stem cells, and dedifferentiated stem cells; blood cells including cord blood, white blood cells, red blood cells, and platelets; and tissue cells including kidney cells, liver cells, and muscle cells, but it is not limited thereto.

In addition, the composition of the present invention may be applicable to all tissues that are commonly used by freezing for preservation, and may include, for example all tissues such as cornea, kidney, heart, small intestine, pancreas, lung, liver, and the like without limitation thereof.

The composition of the present invention may include a cryopreservation liquid for cryopreservation of cells or tissues. The cryopreservation liquid may be water, but it is not limited thereto.

The composition of the present invention may include 0.001 to 0.5% by weight of the nucleic acid structure, and specifically 0.01 to 0.03% by weight, but it is not limited thereto.

While the permeable small molecules used in the current tissue preservation process require a high weight ratio of up to several tens of percent, the nucleic acid origami structure of the present invention may have ice recrystallization inhibition effects even in an extremely low content, which may be more advantageous for preservation of the cells and tissues.

Further, the present invention relates to a method for freezing a cell or tissue including exposing a cell or tissue of a subject to a temperature below zero in the presence of the composition.

When freezing the cells or tissues of the subject in the presence of the composition, it is possible to prevent the cells or tissues from being damaged by inhibiting ice recrystallization at the time of subsequent thawing.

Furthermore, the present invention relates to a composition for freezing a food, and a method for freezing a food including exposing the food to a temperature below zero in the presence of the composition.

The composition of the present invention may be applied to all frozen foods, and when using the composition, it is possible to minimize a decrease in texture of the food at the time of subsequent thawing.

Hereinafter, the present invention will be described in detail with reference to examples.

Example

1. Identification of Ice Recrystallization Inhibition Effect According to Cation and DNA Through Molecular Dynamics Simulation (1) Analysis of Water Molecule Concentration Pattern Around $Mg^{2+}$ Cation First, a change in ice crystal pattern according to $Mg^{2+}$ ion was examined at the molecular level. FIGS. 6 and 7 illustrate arrangements of water molecules around $Mg^{2+}$ ion. The inventors have found that six water molecules (the first shell) initially bound to the $Mg^{2+}$ ion are not easily replaced with other surrounding water molecules, thereby maintaining a unique geometric structure (octahedron) during molecular dynamics (MD) simulation (FIG. 6). In addition, from a more detailed analysis of water molecules around the $Mg^{2+}$ ion, it was found that 12 water molecules are also bound to the second shell (FIG. 7). It is expected that, although binding is not as rigid as that of the first shell, these water molecules present in the second shell are used for ice recrystallization, but play a role of delaying ice recrystallization by decreasing a growth rate of ice crystals. The six water molecules indicated in green are water molecules having the Octahedron structure bound to the first shell, and the remaining water molecules are twelve water molecules around the $Mg^{2+}$ ion bound to the second shell. The ion indicated in blue is the $Mg^{2+}$ ion. The water molecules around the $Mg^{2+}$ ion exist within an $Mg^{2+}$ potential, and thus, it can be seen that, in participating in the surrounding ice recrystallization, it is different from the ice recrystallization of a solution containing only pure water molecules.

(2) Analysis of Effect of Inhibiting Ice Recrystallization in Aqueous Solution

For freely designing the DNA origami structure, it is necessary to reduce the repulsive force between the negative charges of the phosphate groups of the DNA backbone, which requires the use of cations to reduce such a repulsive force.

In order to understand the correlation between DNA origami and ice recrystallization at the molecular level, MD simulation for ice recrystallization was performed according to the concentration and type of ions dissolved in water. In the MD simulation, NAMD package 2.12 and CHARMM force field were used. For effective ice recrystallization, TIP4 was used as a water model.

In order to determine the effects according to the types of ions, three comparative groups, NaCl and $MgCl_2$, and a control (model containing only pure water) were prepared. For comparison according to the concentration of ions, models of 0.01 mol/L, 0.05 mol/L, and 0.15 mol/L of NaCl and $MgCl_2$ solutions were prepared, then MD simulation was performed up to 120 ns, respectively. Herein, the number of water molecules was about 41,500. The simulation was performed at a temperature of 225 K lower than 273K for the rapid ice recrystallization, thereby creating an environment in which ice could grow from an ice seed layer. In order to prevent the ice from being pushed out of the water box during growing due to periodic boundary conditions when the ice grows in all directions, a constraint is applied to some water molecule layers (width=5) below the ice seed layer, thereby allowing the ice to grow in one direction. A prism surface was used as the ice seed.

Referring to FIG. 8, it can be seen that ice growth is inhibited at 225 K by NaCl and $MgCl_2$ compared to the control. The effects of inhibiting ice growth by 50 mM of NaCl and $MgCl_2$, and 150 mM of NaCl and $MgCl_2$ were similarly exhibited. On the other hand, it may be seen that the effect of inhibiting ice growth by $MgCl_2$ is greater than that of NaCl at the concentration of 10 mM of NaCl and $MgCl_2$.

In addition, in order to determine the number of water molecules around $Mg^{2+}$ ion, a radial distribution function (RDF: g(r)) was calculated based on the MD simulation results.

Referring to FIG. 9, the results of the g(r) function shows that six water molecules exist near 2 Å from $Mg^{2+}$ (the first shell), and that the surrounding water molecules also exist at a distance farther than 2 Å. Specifically, four and two water molecules exist near 2.7 Å and 4 Å, respectively, and two water molecules exist at a distance farther than 4 Å.

(3) Simulation of Ice Recrystallization Using Five Types of Different DNA Origami Structures The inventors have identified that $Mg^{2+}$ ion, one of the cations necessary for DNA to be densely concentrated in a form of structure, inhibits ice recrystallization through the MD simulation. Through the identification, it can be seen that the ice recrystallization surface and the distribution of $Mg^{2+}$ ions play an important role in ice recrystallization. Based on this fact, it may be deduced that the DNA origami affects the distribution of surrounding $Mg^{2+}$ ions due to the negative charges of the phosphate groups in the DNA backbone, and as a result, if the DNA origami structures are different from each other, a change in the distribution of $Mg^{2+}$ ions occurs due to the difference structures, and thereby affecting on the ice recrystallization.

In order to verify the deduction, the inventors have simulated five types of DNA bundle structures consisting of two double-stranded DNAs with different origami structures from each other:

(1) 2HB_right1ins (a structure prepared by adding one base to make the DNA bundle be twisted in the right direction ('right-turn structure')).

(2) 2HB_right2ins (a structure prepared by adding two bases to make the DNA bundle be twisted in the right direction).

(3) 2HB_left1del (a structure prepared by removing one base to make the DNA bundle be twisted in the left direction ('left-turn structure')).

(4) 2HB_left2del (a structure prepared by removing the two bases to make the DNA bundle be twisted in the left direction).

(5) 2HB straight (a bundle structure without twisting)

These DNA structures are structures having almost the same length, and are subjected to a change in the twisting direction of the DNA bundle. In order to determine whether these five different structures effect the ice recrystallization through the MD simulation, ice fraction, distribution of $Mg^{2+}$ ions around the DNA origami structure, root mean square deviation (RMSD) and solvent accessible surface area (SASA) of DNA backbone, etc. were measured. As similar to the previous experiment, the MD simulation was performed for 40 ns under 10 mM $MgCl_2$ ion environment at a temperature of 225 K (FIG. 10).

In a direction of looking down on the ICE seed layer from the top, the graphs show the structures by colors, wherein 2HB straight is black, 2HB_right1ins is red, 2HB_right2ins is yellow, 2HB_left1del is blue, and 2HB_left2del is green.

1) RMSD

The left-turn structures are characterized by having larger RMSD values (FIG. 11). These structures exhibited RMSD change two times or more than those of the straight and right-turn structures. Considering that the helix direction of the canonical DNA is the right side, it can be believed that more torsion energy was generated when designing the DNA origami having the left-turn helix structure. It can be interpreted that such a structure exhibits a larger change in RMSD during dynamic relaxation in the solution.

2) Solvent-Accessible Surface Area (SASA) and $Mg^{2+}$ Ions Around DNA

SASA means a value of how much surface area of protein or DNA, etc. is exposed to a solvent. In relation to calculation results, the inventors have expected that, as the value of the SASA is increased, the DNA backbone is more exposed to the solvent, and $Mg^{2+}$ ions are more collected in the DNA structure. In order to verify this expectation, the number of $Mg^{2+}$ ions according to the distance from the DNA backbone was calculated, and then the distributions of $Mg^{2+}$ ions were compared for five types of different structures. As a result of calculations the SASA and $Mg^{2+}$ ion distribution, it was confirmed that the largest number of $Mg^{2+}$ ions was collected within 10 Å from the backbone of the structure having the largest SASA. It was deduced that, according to the different structures of DNA origami, the distribution of $Mg^{2+}$ ions, which are differently distributed near the DNA backbone (10 Å), would have different effects on the ice recrystallization.

In the SASA calculation, the used "probe radius" was 1.4 Å. The 2HB_right2ins structure exhibited the largest SASA and also exhibited significant changes over time. On the other hand, two structures of 2HB_left1del and 2HB_left2del, which are designed as the left-turn structure, exhibited relatively smaller SASA values than the other structures. Among them, the 2HB_left2del structure exhibited the smallest SASA among SASAs of five different structures (FIG. 12).

The number of $Mg^{2+}$ ions within 10 Å from the DNA backbone was calculated to have the highest number of $Mg^{2+}$ ions near the 2HB_right2ins structure, in an order similar to the SASA results. On the other hand, the number of $Mg^{2+}$ ions around two structures of 2HB_left1del and 2HB_left2del, which are designed as the left-turn structure, was calculated to be relatively smaller than the other structures. Among them, the number of $Mg^{2+}$ ions around the 2HB_left1del structure was the smallest value among the numbers of $Mg^{2+}$ ions of five different structures (FIG. 13).

FIG. 14 illustrates initial structures (0 ns) and dynamically relaxed structures at 40 ns of five different structures. In addition, the distribution of $Mg^{2+}$ ions within 10 Å in the DNA backbone structure was illustrated together. The graphs show the structures by colors, wherein 2HB straight is black, 2HB_right1ins is red, 2HB_right2ins is yellow, 2HB_left1del is blue, and 2HB_left2del is green.

It can be seen that the DNA structures prepared in the right-turn structure have increased distances between the DNA backbones relative to the initial structures (0 ns). It is believed that these DNA origami structures prepared in the right-turn structure have increased SASA values due to the increased (open) gaps between the DNA backbones. In addition, it can be seen that the number of $Mg^{2+}$ ions within 10 Å from the DNA backbone is increased due to the $Mg^{2+}$ ions collected in the open gaps. On the other hand, it can be seen that, although the DNA origami structures prepared in the left-turn structure show large changes in RMSD, from a structure of achieving dynamic equilibrium at 40 ns, the large values of RMSD are mainly caused by a change in the structure due to the rotation related to a torsion energy for the initial structure (0 ns), and in fact, the gap between the DNA backbones is rather decreased (closed). It can also be seen that the left-turn structures have relatively smaller SASA values than the right-turn structures, despite the large changes in the RMSD.

3) Ice Fraction

The 2HB_left2del (Green) having the smallest SASA value exhibited the slowest ice recrystallization, followed by 2HB_left1del (Blue) in terms of ice recrystallization inhibition. That is, since the gaps between the DNA backbone structures are not relatively largely increased, the structures having the smallest number of $Mg^{2+}$ ions within 10 Å from the DNA backbone show that the ice recrystallization was most inhibited. On the other hand, the structures of 2HB_right1ins (Red) and 2HB_right2ins (Orange), which have the highest SASA value and the largest number of $Mg^{2+}$ ions within 10 Å, had relatively less ice recrystallization inhibition than the other structures (FIG. 15).

(4) Simulation of Ice Recrystallization Using Different DNA Origami Structures of Megastructure Through the above MD simulation, the correlation between ice recrystallization rates according to various twisting directions and degrees of DNA structures was deduced. In order to observe the clearer difference, four types of structures, which have the same cross-section but are largely different in the shape, were designed.
1) Circular DNA bundle structure
2) Straight DNA bundle structure
3) Curved DNA bundle structure
4) A system in which a contact surface between the annular DNA bundle structure and the ice surface is changed (named as a Circle_side).

In order to determine whether these four different structures effect the ice recrystallization through the MD simulation, ice fraction, distribution of $Mg^{2+}$ ions around the DNA origami structure, root mean square deviation (RMSD) and solvent accessible surface area (SASA) of DNA backbone, etc. were measured. As similar to the previous experiment, the MD simulation was performed for 30 ns under 10 mM $MgCl_2$ ion environment at a temperature of 225 K.

System size: Number of atoms
Circular DNA bundle structure: 1,333,311
Curved DNA bundle structure: 1,430,960
Straight DNA bundle structure: 1,290,309
Circle_side DNA bundle structure: 1,881,446

Referring to FIGS. 16 to 23, it can be confirmed that DNA structures inhibit ice recrystallization, and structures having a high area adjacent to the ice recrystallization surface exhibit higher growth inhibition rates than the other structures.

FIGS. 24 to 27 illustrate the distributions of $Mg^{2+}$ ions from each DNA backbone by the numbers thereof.

FIG. 28 illustrates RMSD values for four types of DNA origami structures for 20 ns. The circular DNA origami structure exhibited the largest change in RMSD, followed by the Circle_side DNA origami structure. The circular DNA origami structure exhibits a significant change in RMSD through dynamic relaxation of the torsion energy stored therein.

FIG. 29 illustrates changes in SASA of the four types DNA origami structures. The Circular DNA structure and the Circle_side structure exhibited the largest change in SASA over time.

FIG. 30 illustrates ice fraction results, wherein the ice recrystallization of circular DNA origami structure was most inhibited. On the other hand, the Circle_side DNA origami structure exhibited the largest ice recrystallization. The results show that the distance between the DNA origami structure and the ice recrystallization plane is relatively large, such that the contact surface of the DNA structure does not significantly affect the ice growth. That is, in order for the DNA origami structure to inhibit ice recrystallization, it is important to effectively come into contact with ice crystal surfaces having various sizes and directions in a state of containing cations. To this end, it can be expected that the DNA structure need to be densely packed in a state of having constant shape and rigidity.

2. Identification of Ice Recrystallization Inhibition Effect by Cation and DNA Structure Through Experiment Following the identification of the ice recrystallization inhibition (RI) effect by the cation and DNA strands at the molecular level, a series of experiments were conducted to observe the RI effect through actual macroscopic observation.

(1) Experiment Method for Ice Recrystallization

A splat cooling experimental technique commonly known in the art was used to measure the RI effect (FIG. 31). First, a cover glass was placed on a metal plate pre-cooled with liquid nitrogen (temperature on cover glass surface is about −150° C.), and 20 µl of a solution containing a material for measuring the RI effect dispersed therein was dropped at a height of about 1.5 m. As soon as the solution contacts the cover glass, it spreads thinly and freezes while being rapidly cooled, and a plurality of very small ice crystals are formed due to the rapid cooling. Then, the cover glass was transferred to a cold stage having drilled holes through which ice crystals can be observed with an optical microscope. The cold stage was maintained at −6° C., and a state, in which the ice crystals grow as small crystals gradually merge, was observed for 30 minutes. Thereafter, the sizes of the ice crystals were measured to compare how much the ice crystals have less grown compared to the control group (a sample containing only solution without a freezing control material).

(2) Observation of RI Effect in Cations-Containing Aqueous Solution and Unstructured DNA Sample First, RI measurement experiment was performed on a buffer solution containing only $MgCl_2$ in pure distilled water, and it was confirmed that ice recrystallization was inhibited as the ion concentration was increased (FIGS. 32 and 33). Based on the results of this experiment, the $MgCl_2$ concentration of the reference buffer solution in the subsequent experiments was set to be 5 mmol (mM). RI performance of the sample was measured by comparing relative RI performance of the sample to the reference buffer, which means that the smaller value, the higher RI performance.

Next, RI measurement experiment was performed on a solution containing DNA in the unstructured single-stranded state. The concentration of DNA used in the experiment was set to be 50 to 200 ng/uL, which is similar to the concentration of DNA structures prepared through the conventional manufacturing processes. As a result of measuring the RI performance of a sample in which 169 types of staple DNAs forming 6 helix bundle rigid structure are mixed in a single-stranded state, it was observed to have a value of 0.87 to 1.0 with little ice recrystallization inhibition effect compared to the buffer (FIGS. 34 and 35). In other words, it was experimentally confirmed that, although DNA strands have the effect of aggregating $Mg^{2+}$ ions, it is impossible to hold the $Mg^{2+}$ ions unless they form a structure having a constant shape and rigidity in an aqueous solution, thereby the RI effect hardly occurs at the macro level.

In addition, the RI value of the scaffold DNA sample performed in the same manner was measured up to about 0.7 (FIGS. 36 and 37). The reason why the scaffold DNA has a slight RI performance compared to the staple DNA is assumed that, due to characteristics of the long scaffold DNA, it forms a secondary structure in which the entire region does not exist in the single-stranded state, but rather some portions bind in a double strand with complementary to each other.

(3) Design of Structured DNA Origami

Thereafter, an experiment was performed on a DNA structure in which DNA strands are densely linked to each other thus to have constant cross-sectional shape and rigidity. 9 types of structures designed as an example of DNA origami technique include: (1) 4 helix bundle rigid structure; (2) 4 helix bundle flexible structure (gap 5 nt); (3) 6 helix bundle rigidity structure; (4) 6 helix bundle flexible structure (gap 3 nt); (5) 6 helix bundle flexible structure (gap 5 nt); (6) Rothemund square structure; (7) 12 helix bundle rigid structure; (8) 12 helix bundle bent structure (90°); and (9) 12 helix bundle bent structure (45°).

The design methods for each structure are as follows.

(1) 4 helix bundle rigid structure and (2) 4 helix bundle flexible structure (gap 5 nt)

The structures (1) and (2) have cross sections consisting of four double-stranded DNAs, of which one side is packed in a square shape of about 4.5 nm (FIG. 38). These have a structure in which the same forms of linkage are repeated based on a length of about 192 nt, and have a total length of about 600 nm, respectively. The rigid structure of (1) was designed so that opposite ends of all staple DNAs present in the structure are directly contact with each other, and the flexible structure of (2) consists of ssDNA in which a gap between opposite ends of 150 adjacent staple DNAs is 5 nt.

(3) 6 helix bundle rigid structure, (4) 6 helix bundle flexible structure (gap 3 nt) and (5) 6 helix bundle flexible structure (gap 5 nt)

The structures (3), (4) and (5) have cross sections consisting of six double-stranded DNAs, which are packed in a hexagonal shape (FIG. 39). These have a structure in which the same forms of linkage are repeated based on a length of about 168 nt, and have a total length of about 400 nm, respectively. The rigid structure of (3) was designed so that opposite ends of all staple DNAs present in the structure are directly contact with each other, and the flexible structures of (4) and (5) consist of ssDNA in which a gap between opposite ends of 169 adjacent staple DNAs is 3 nt and 5 nt, respectively.

(6) Rotemund Square

The structure (6) has a cross section consisting of twenty four double-stranded DNAs, which are arranged in a straight line to form a sheet shape (FIG. 40). The structure has a length of about 90 nm and a width of about 55 nm based on at 256 nt. This structure was designed so that all ends of the 192 staple DNA present in the structure directly contact with each other.

(7) 12 helix bundle rigid structure, (8) 12 helix bundle bent structure (90°), (9) 12 helix bundle bent structure (45°)

The structures (7), (8), and (9) have cross sections consisting of twelve double-stranded DNAs, which are packed in a hexagonal shape (FIG. 41). The rigid structure of (7) was designed so that all ends of 180 staple DNAs directly contact with each other. The structures (8) and (9) have flexible regions with a length of 42 nt by removing 11 staple DNAs present in the middle of the structure, and are formed in a shape in which the length of the DNA linking opposite ends of the structure was shortened to 357 nt and 189 nt, respectively, and a central portion thereof was bent at 90° and 45°, respectively.

(4) Preparation of DNA Origami and Observation of RI Effect

Thereafter, the ice recrystallization inhibition effect of DNA structure structured so as to have constant cross-sectional shape and size was confirmed. The shape of the structure prepared according to the above design was measured by atomic force microscopy (first column images of FIGS. 42, 43 and 44). As a result of performing RI experiments on at least nine types of DNA structures having at least two types of different densities, RI value with a maximum of 0.53 was measured (FIG. 45). The remaining samples exhibited higher RI performance than 4 helix bundle (samples 1 and 2) having the narrowest cross-sectional area, and the higher the concentration of the structure, the higher RI performance as a whole. This is believed that since the $Mg^{2+}$ ions can be sufficiently aggregated so that the RI performance may be exhibited when the cross-sectional area is at a certain level, and as the number of structures in the aqueous solution is increased, a region capable of inhibiting ice recrystallization is increased.

Through a series of experiments, it was demonstrated that the composition including the DNA structures in which cations were aggregated could exert higher ice recrystallization inhibition effects than DNA which does not form a structure.

What is claimed is:

1. A method for inhibiting ice recrystallization, the method comprising applying a composition comprising a nucleic acid structure comprising a scaffold nucleic acid folded at predetermined positions to form a plurality of strands, and a plurality of staple nucleic acids, wherein at least a portion thereof has a complementary sequence to at least a portion of the scaffold nucleic acid, thereby binding to the scaffold nucleic acid to form a double strand to a cell or tissue.

2. The method according to claim 1, wherein the nucleic acid structure comprises a cation bound to at least a portion of negative charges thereof.

3. The method according to claim 2, wherein the cation bound to the nucleic acid structure is $Na^+$, $NH_4^+$, or $Mg^{2+}$.

4. The method according to claim 1, wherein the nucleic acid structure comprises a surface which includes at least two helix bundles and is configured to come into contact with ice crystals.

5. The method according to claim 1, wherein at least one of the helices of the nucleic acid structure has a gap which is formed in at least a portion thereof with a single strand.

6. The method according to claim 1, wherein the nucleic acid structure has a twisted or curved helix bundle.

* * * * *